US009717412B2

(12) United States Patent
Roham et al.

(10) Patent No.: US 9,717,412 B2
(45) Date of Patent: Aug. 1, 2017

(54) WIRELESS FETAL MONITORING SYSTEM

(75) Inventors: Masoud Roham, San Diego, CA (US); Enrique Saldivar, Santee, CA (US); Srinivas Raghavan, San Diego, CA (US); Mehran Mehregany, San Diego, CA (US); Mitul Shah, San Diego, CA (US)

(73) Assignee: GARY AND MARY WEST HEALTH INSTITUTE, San Diego, CA (US)

( * ) Notice: Subject to any disclaimer, the term of this patent is extended or adjusted under 35 U.S.C. 154(b) by 0 days.

(21) Appl. No.: 13/290,002

(22) Filed: Nov. 4, 2011

(65) Prior Publication Data
US 2012/0232398 A1 Sep. 13, 2012

Related U.S. Application Data

(60) Provisional application No. 61/410,803, filed on Nov. 5, 2010, provisional application No. 61/410,793, filed
(Continued)

(51) Int. Cl.
*A61B 8/00* (2006.01)
*A61B 5/00* (2006.01)
(Continued)

(52) U.S. Cl.
CPC ........ *A61B 5/0011* (2013.01); *A61B 5/02411* (2013.01); *A61B 8/0866* (2013.01);
(Continued)

(58) Field of Classification Search
CPC ..... A61B 8/0866; A61B 8/565; A61B 5/0011; A61B 5/0022
(Continued)

(56) References Cited

U.S. PATENT DOCUMENTS 4,228,506 A * 10/1980 Ripley ................ G06F 19/3406
346/33 ME
4,248,244 A * 2/1981 Charnitski ........... A61B 5/0404
600/519
(Continued)

FOREIGN PATENT DOCUMENTS

EP 1097672 A1 5/2001
WO WO 2009/073123 A1 6/2009

OTHER PUBLICATIONS

Advanced Pharma, "Huntleigh Tele-Fetal Monitors" as of Apr. 2011, 2 pages. http://www.advanced-pharma.com/fetalmonitors.html, © 2004.
(Continued)

*Primary Examiner* — Rajeev Siripurapu
(74) *Attorney, Agent, or Firm* — David B. Murphy; O'Melveny & Myers LLP

(57) ABSTRACT

A wireless fetal and maternal monitoring system includes a fetal sensor unit adapted to receive signals indicative of a fetal heartbeat, the sensor optionally utilizing a Doppler ultrasound sensor. A short-range transmission unit sends the signals indicative of fetal heartbeat to a gateway unit, either directly or via an auxiliary communications unit, in which case the electrical coupling between the short-range transmission unit and the auxiliary communications unit is via a wired connection. The system includes a contraction actuator actuatable upon a maternal uterine contraction, which optionally is a EMG sensor. A gateway device provides for data visualization and data securitization. The gateway device provides for remote transmission of information through a data communication network. A server adapted to receive the information from the gateway device serves to store and process the data, and an interface system to permits remote patient monitoring.

28 Claims, 17 Drawing Sheets

Related U.S. Application Data on Nov. 5, 2010, provisional application No. 61/454,896, filed on Mar. 21, 2011, provisional application No. 61/488,334, filed on May 20, 2011.

(51) Int. Cl.
*A61B 8/08* (2006.01)
*A61B 5/024* (2006.01)
*A61B 5/0245* (2006.01)
*A61B 5/03* (2006.01)
*A61B 5/0488* (2006.01)

(52) U.S. Cl.
CPC .......... *A61B 8/4227* (2013.01); *A61B 8/4472* (2013.01); *A61B 8/488* (2013.01); *A61B 8/565* (2013.01); *A61B 5/0022* (2013.01); *A61B 5/0245* (2013.01); *A61B 5/02438* (2013.01); *A61B 5/02444* (2013.01); *A61B 5/033* (2013.01); *A61B 5/04882* (2013.01); *A61B 5/4356* (2013.01); *A61B 5/6832* (2013.01)

(58) Field of Classification Search
USPC ......................................................... 600/453
See application file for complete search history.

(56) References Cited

U.S. PATENT DOCUMENTS

| | | | |
|---|---|---|---|
| 4,640,295 A * | 2/1987 | Isaacson | 600/561 |
| 4,783,813 A * | 11/1988 | Kempka | A61B 7/04 381/67 |
| 5,257,627 A * | 11/1993 | Rapoport | 600/437 |
| 5,363,857 A | 11/1994 | Howard | |
| 5,544,665 A | 8/1996 | Litovitz et al. | |
| 5,807,271 A | 9/1998 | Tayebi et al. | |
| 5,817,035 A | 10/1998 | Sullivan | |
| 5,882,300 A | 3/1999 | Malinouskas et al. | |
| 6,115,624 A | 9/2000 | Lewis et al. | |
| 6,264,614 B1 | 7/2001 | Albert et al. | |
| 6,416,471 B1 * | 7/2002 | Kumar et al. | 600/300 |
| 6,781,522 B2 | 8/2004 | Sleva et al. | |
| 6,995,650 B2 | 2/2006 | Hayashi et al. | |
| 7,162,278 B2 | 1/2007 | Vanselous | |
| 7,257,438 B2 | 8/2007 | Kinast | |
| 7,277,745 B2 | 10/2007 | Natarajan et al. | |
| 7,333,850 B2 | 2/2008 | Marossero et al. | |
| 7,470,232 B2 * | 12/2008 | Hoctor et al. | 600/453 |
| 7,532,923 B1 | 5/2009 | Hayes-Gill et al. | |
| 7,593,765 B2 | 9/2009 | Rapoport et al. | |
| 7,758,522 B2 | 7/2010 | Pandit | |
| 7,764,996 B2 | 7/2010 | Zhang et al. | |
| 7,865,233 B2 | 1/2011 | Haefner | |
| 7,976,480 B2 | 7/2011 | Grajales et al. | |
| 8,066,379 B2 | 11/2011 | Lalley et al. | |
| 8,116,841 B2 | 2/2012 | Bly et al. | |
| 8,116,855 B2 | 2/2012 | James et al. | |
| 8,125,440 B2 | 2/2012 | Guyot-Sionnest et al. | |
| 8,229,550 B2 | 7/2012 | James et al. | |
| 8,255,238 B2 | 8/2012 | Powell et al. | |
| 8,273,370 B2 | 9/2012 | Harima et al. | |
| 8,280,484 B2 | 10/2012 | Boyden et al. | |
| 8,301,232 B2 | 10/2012 | Albert et al. | |
| 8,332,021 B2 | 12/2012 | Vullings et al. | |
| 8,348,841 B2 | 1/2013 | Varadan | |
| 2002/0193670 A1 * | 12/2002 | Garfield | A61B 5/0444 600/304 |
| 2003/0038047 A1 * | 2/2003 | Sleva et al. | 206/370 |
| 2004/0019288 A1 * | 1/2004 | Kinast | 600/509 |
| 2004/0203354 A1 * | 10/2004 | Yue | 455/41.1 |
| 2005/0102167 A1 * | 5/2005 | Kapoor | 705/3 |
| 2006/0089541 A1 * | 4/2006 | Braun | G06F 19/3406 600/300 |
| 2007/0016089 A1 | 1/2007 | Fischell et al. | |
| 2007/0106133 A1 | 5/2007 | Satchwell et al. | |
| 2007/0127759 A1 | 6/2007 | Zhang et al. | |
| 2007/0149887 A1 | 6/2007 | Hwang et al. | |
| 2007/0191728 A1 | 8/2007 | Shennib | |
| 2007/0208252 A1 | 9/2007 | Makower | |
| 2007/0213627 A1 * | 9/2007 | James et al. | 600/511 |
| 2007/0260154 A1 * | 11/2007 | Rapoport et al. | 600/528 |
| 2007/0299349 A1 | 12/2007 | Alt et al. | |
| 2008/0039744 A1 * | 2/2008 | Hamilton | 600/588 |
| 2008/0064980 A1 | 3/2008 | Lee et al. | |
| 2008/0114224 A1 | 5/2008 | Bandy et al. | |
| 2008/0119705 A1 | 5/2008 | Patel et al. | |
| 2008/0161689 A1 * | 7/2008 | Pandit | 600/438 |
| 2008/0208009 A1 * | 8/2008 | Shklarski | 600/301 |
| 2008/0319294 A1 | 12/2008 | Taub | |
| 2009/0076363 A1 * | 3/2009 | Bly et al. | 600/372 |
| 2009/0143650 A1 | 6/2009 | Guion-Johnson | |
| 2009/0303098 A1 | 12/2009 | Wilkins | |
| 2010/0049050 A1 | 2/2010 | Pelissler et al. | |
| 2010/0106519 A1 | 4/2010 | Lemke et al. | |
| 2010/0274145 A1 | 10/2010 | Tupin, Jr. et al. | |
| 2011/0077526 A1 | 3/2011 | Zwirn | |
| 2011/0137209 A1 | 6/2011 | Lahiji et al. | |
| 2012/0065479 A1 | 3/2012 | Lahiji et al. | |
| 2012/0150010 A1 | 6/2012 | Hayes-Gill et al. | |
| 2012/0232398 A1 | 9/2012 | Roham et al. | |

OTHER PUBLICATIONS

Ayat, et al., "Prototype of a Standalone Fetal ECG Monitor," 2010 IEEE Symposium on Industrial Electronics and Applications (ISIEA 2010), Oct. 3-5, 2010, pp. 617-622.

Azhim, et al., "Monitoring Carotid Blood Flow and ECG for Cardiovascular Disease in Elder Subjects," Engineering in Medicine and Biology Society, 2005, IEEE-EMBS, 2005, 27th Annual International Conference of the 2005, Sep. 1-4, 2005, pp. 5495-5498.

Baby Beat, About Us—Who is Baby Beat?, as of Apr. 2011, 2 pages. http://www.babybeat.com/about-babybeat.html.

Barth, et al., "Tempo 3.1: A Body Area Sensor Network Platform for Continuous Movement Assessment", Wearable and Implantable Body Sensor Networks, 2009, BSN 2009, Sixth International Workshop, 2009, pp. 71-76.

Byl, et al., "Incisional Wound Healing: A Controlled Study of Low and High Dose Ultrasound", JOSPT, vol. 18, No. 5, Nov. 1993, pp. 619-628.

Chen, et al., "A Comparative Study of a New Cardiotocography Analysis Program," Engineering in Medicine and Biology Society, 31$^{st}$ Annual International Conference of the IEEE EMBS, Sep. 2-6, 2009, pp. 2567-2570.

Chou, et al., "Radio Frequency Electromagnetic Exposure: Tutorial Review on Experimental Dosimetry", Bioelectricmagnetics, vol. 17, issue 3, 1996, pp. 195-208.

Cox, "Top-Rated Cell Phones Also Rank High in Radiation Emissions", Network World, Feb. 24, 2010, 3 pages. http://www.pcworld.idg.com.au article/337324/top-rated_cell_phones_also_rank_high_rad . . .

Espina, et al., Wireless Body Sensor Network for Continuous Cuff-less Blood Pressure Monitoring, Proceedings of the 3$^{rd}$ IEEE-EMBS, Internatioal Summer School and symposium on Medical Devices and Biosensors, MIT, Sep. 4-6, 2006, pp. 11-15.

Federal Office of Public Health (FOPH), "Bluetooth", last updated on Jan. 30, 2007, 4 pages. http://www.bag.admin.ch/themen/strahlung/00053/00673/03571/index.html?lang=en.

Fitzpatrick, "Ultrasound imaging now possible with a smartphone," Apr. 20, 2009, 2 pages. http://news-info.wustl.edu/tips/page/normal/13928.html.

GE Healthcare, Ultrasound for Vascular Imaging, as of Apr. 2011, 3 pages. http://www.gehealthcare.com/usen/ultrasound/genimg/products/vascular.htm, © 2010.

GE Healthcare, Ultrasound Product Information, as of Apr. 2011, 2 pages. https://www2.gehealthcare.com/portal/site/usen/menuitem.0668199d894d51503806171047b29330/?vgnextoid=dd3ba52fcea2d110VgnVCM100000258c1403RCRD&vgnextfmt=defaul, © 2011.

(56) References Cited

OTHER PUBLICATIONS

GE, Vscan pocket-sized, ultra-smart ultrasound unveiled, Oct. 20, 2009, 3 pages. http://www.gereports.comJvscan-pocket-sized-ultra-smart-ultrasound-unveiled.

GE Healthcare, For the Obstetrics Patient overview of Obstetrics Ultrasound products, as of Apr. 2011, 1 page. http://www.gehealthcare.com/usen/patient/ultrasound/aboutvoluson.html, © 2010.

Ghasemzadeh, et al., "A Greedy Buffer Allocation Algorithm for Power-Aware Communication in Body Sensor Networks", Proceedings of the Eighth IEEE/ACM/IFIP International Conference on Hardware/Software Codesign and System Synthesis, ser. CODES/ISSS '10, New York, N.Y., USA: ACM, 2010, pp. 195-204.

Ghasemzadeh, et al., "Structural Action Recognition in Body Sensor Networks: Distributed Classification Based on String Matching,", IEEE Transactions on Information Technology in Biomedicine, vol. 14, No. 2, Mar. 2010, pp. 425-435.

Gussenhoven, et al., "Arterial Wall Characteristics Determined by Intravascular Ultrasound Imaging: An in Vitro Study," Journal of the American College of Cardiology, vol. 14. No. 4, Oct. 1989, pp. 947-952.

Haider, "Power Drive Circuits for Diagnostic Medical Ultrasound", Proceedings of the 18th International Symposium on Power Semiconductor Devices & IC's, Jun. 4-6, 2006 8 pages.

Henderson, et al., "A Portable High-intensity Focused Ultrasound Device for Noninvasive Venous Ablation", Journal of Vascular Surgery, 2009, pp. 1-5.

Jafari, et al., "Medical Embedded Systems", Embedded System Design Topics, Techniques and Trends, IFIP Advances in Information and Communication Technology, vol. 231, 2007, pp. 441-444.

Jun, et al., "Wearable ECG Recognition & Monitor", Proceedings of the 18$^{th}$ IEEE Symposium on Computer-Based Medical Systems (CBMS'05), 2005, 6 pages.

Leonov, et al., "Thermoelectric Mems-Generators as a Power Supply for a Body Area Network",The 13$^{th}$ International Conference on Solid-State Sensors, Actuators and Microsystems, vol. 1, Jun. 5-9, 2005, pp. 291-294.

LGMEDSUPPLY.com, Professional Ultrasound Unit for Ultrasound Therapy, as of Apr. 2011, 5 pages. http://www.lgmedsupply.com/lgpoulun.html.

Miller, "Two-mic system detects fetal heart rate anomalies, prenatal beat sampling,", 2009, 4 pages. http://www.engadget.com/2009/08/30/two-mic-system-detects-fetal-heart-rate-anomalies-prenatal-beat.

NCC (National Certification Corporation), "NICHD Definitions and Classifications: Application to Electronic Fetal Monitoring Interpretation", NCC Monograph, vol. 3, No. 1, 2010, pp. 1-20.

Park, et al., An Ultra-Wearable Wireless, Low Power ECG Monitoring System, Biomedical Circuits and Systems Conference, 2006, BioCAS, IEEE, Dec. 2006, pp. 241-244.

Schlembach, et al., "Monitoring the Progress of Pregnancy and Labor using Electromyography", European Journal of Obstetrics & Gynecology and Reproductive Biology, vol. 144, Supp. 1, 2009, pp. S33-S39.

Sheehan, et al., "Expert visual guidance of ultrasound for telemedicine", J Telemed Telecare, vol. 16, No. 2, 2010, pp. 77-82.

SONOSITE.com, Portable Diagnostic Ultrasound Machines as of Apr. 2011, 2 pages. http://www.sonosite.com/products/portable-ultrasound/.

Sweha, et al., "Interpretation of the Electronic Fetal Heart Rate During Labor", American Family Physician, vol. 59, issue 9, May 1, 1999, pp. 2487-2500.

USEDULTRASOUND.com, "Acuson P40 Ultrasound System" as of Apr. 2011, 2 pages. http://www.usedultrasound.com/ultrasound-systems/acuson/acuson-p10-ultrasound-system.

van Geijn, "Cardiotocography", in Textbook of Perinatal Medicine, Parthenon Publishing, 1998, vol. 2, pp. 1424-1428. http://www.obgyn.net/displayarticle.asp?page=/fm/articles/cardiotocographya998-def.

WIKIPEDIA.org, "Specific Absorption Rate", as of Jul. 24, 2013, 4 pages. http://en.wikipedia.org/wiki/Specific_absorption_rate.

Wildstrom, "Bluetooth: Dangerous Waves?", Bloomberg Businessweek, Apr. 27, 2005, 3 pages,http://www.businessweek.com/technology/content/apr2005.tc20050427-5651.htm.

Willacy, et al., "Intrapartum Fetal Monitoring", Patient.co.uk, emis, document ID: 1063, version 23, last checked Dec. 20, 2010, 6 pages.

World Health Organization, "Electromagnetic Fields and Public Health: Mobile Phones", Fact sheet No. 193, Jun. 2011, 4 pages, http://www/who.int/mediacentre/factsheets/fs193/en/.

Xiao et al., "Transmission Power Control in Body Area Sensor Networks for Healthcare Monitoring", IEEE Journal on Selected Areas in Communications, 2009, vol. 27, No. 1, pp. 37-48.

Zappi, et al., "Activity Recognition from On-Body Sensors: Accuracy-Power Trade-Off by Dynamic Sensor Selection", EWSN 2008, LNCS 4913, 2008, pp. 17-33.

European Search Report re EP 11 83 8953 dated Apr. 1, 2014.

\* cited by examiner

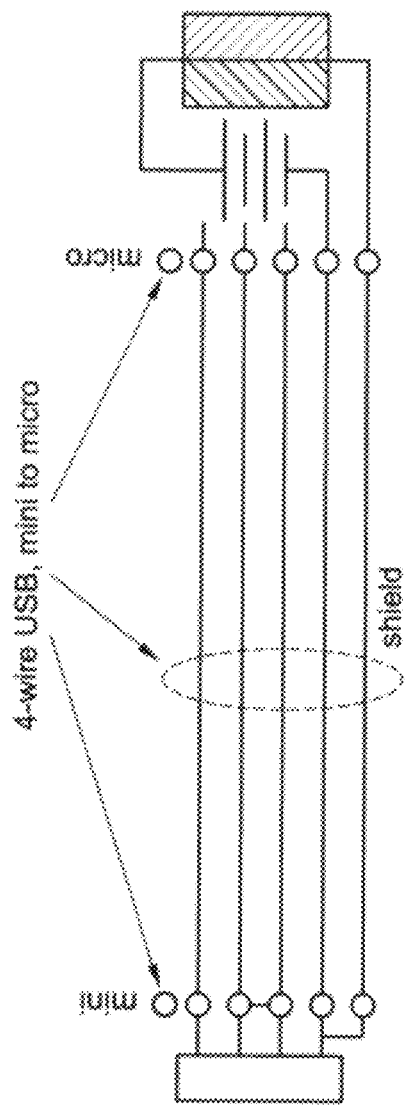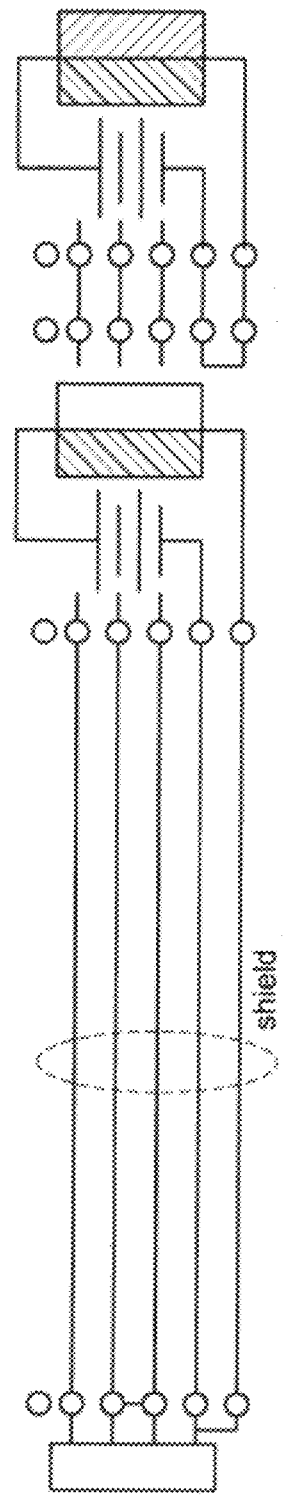
FIG. 10A
FIG. 10B

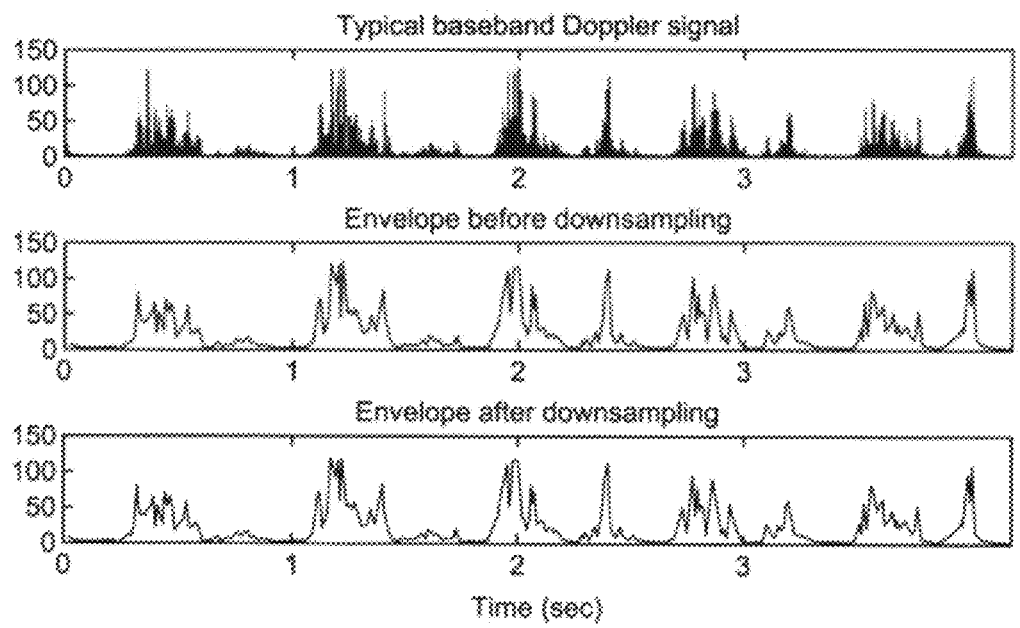
FIG. 11
| SYNCH (events) | TOCO | FHR0 (primary) | FHR1 (twin) |
FIG. 12A
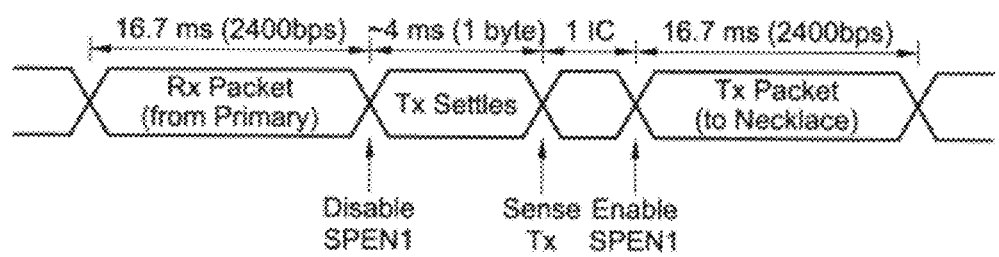
FIG. 12B

WIRELESS FETAL MONITORING SYSTEM

PRIORITY CLAIM

This application claims priority to U.S. Provisional Application No. 61/410,803, filed Nov. 5, 2010, entitled "Wireless Fetal Monitoring System", U.S. Provisional Application No. 61/410,793, filed Nov. 5, 2010, entitled "Electronic Data Capture, Documentation, and Clinical Decision Support System", U.S. Provisional Application No. 61/454,896, filed Mar. 21, 2011, entitled "Prenatal Wireless Mobile Pack", and U.S. Provisional Application No. 61/488,334, filed May 20, 2011, entitled "Low-Cost Portable Fetal Monitor With Provisions for Multiple Births", all of which are incorporated herein by reference as if fully set forth herein.

STATEMENT OF RELATED APPLICATIONS

This application is related to U.S. Published Patent Application 2011/0137209, Ser. No. 12/917,848, filed Nov. 2, 2010, entitled "Microphone Arrays for Listening to Internal Organs of the Body", U.S. patent application Ser. No. 13/094,678, filed Apr. 26, 2011, entitled "Ultrasound Patch", U.S. Patent Application Ser. No. 61/410,793, filed Nov. 5, 2010, entitled "Electronic Data Capture, Documentation and Clinical Decision Support System", and U.S. patent application Ser. No. 13/102,817, filed May 6, 2011, entitled "Multipurpose, Modular Platform for Mobile Medical Instrumentation", all of which are incorporated herein by reference as if fully set forth herein.

FIELD OF THE INVENTION

The present invention relates to fetal and maternal monitoring systems, particularly those to monitor for fetal distress. More particularly, the systems, devices, apparatus and methods relate to improved monitoring systems with enhanced functionality for wireless fetal monitoring systems.

BACKGROUND OF THE INVENTION

Fetal Distress Syndrome is an abnormal condition during gestation or at the time of delivery, marked by altered heart rate or rhythm and leading to compromised blood flow or changes in blood chemistry. Detection of fetal distress syndrome is done in obstetrics by Cardiotocography, the simultaneous measurement of fetal heart rate and uterine contractions. The change in fetal heart rate as a response to uterine contractions is the diagnostic basis of fetal distress syndrome. See, e.g., "Cardiotocography", van Geijn, H. P., Textbook of Perinatal Medicine, Parthenon Publishing, 1998, Vol. 2, p. 1424-8. In every-day obstetrics practice, physicians routinely prescribe cardiotocograms to detect fetal distress syndrome.

Cardiotocography, or electronic fetal monitoring (EFM), is a common non-invasive diagnostic technique utilized in obstetrics to detect and determine the extent of Fetal Distress Syndrome. Cardiotocography uses the simultaneous measurement of the fetal heart rate ("cardio") and the uterine contractions ("toco") to detect any abnormalities.

Current technology is composed of a central unit, which contains a printer, a Doppler fetal monitor (to register the fetal heart rate), and a tocodynamometer (to register uterine contractions). In currently used equipment, the sensors are affixed to the abdomen of the mother and connected to the central unit via connecting cables.

Typically, a conventional tocodynamometer is a strain gauge attached to a belt around the abdomen of the patient. The strain gauge detects the tension on the uterus wall during contractions. Also conventionally, a Doppler ultrasound transducer measures fetal heart rate. The result is a graphical overlay of both measurements, seen either on a screen or on paper. By comparing changes in fetal heart rate to maternal contractions, the healthcare provider assesses the status of the fetus and determines if fetal distress is present.

Currently, obstetric patients requiring EFM are referred to either a hospital or outpatient clinic setting where monitoring takes place under the physical presence of a technician or nurse. While resting in bed, the sensors are placed on the patient and the sensors are connected to a measuring apparatus with cables, thus limiting the patient's mobility. The measuring apparatus displays two simultaneous graphs, one with the fetal heart rate and the other with the uterine contractions (on paper or screen). The practitioner determines the presence and the severity of Fetal Distress Syndrome based on these two graphs. See, e.g., "Interpretation of the Electronic Fetal Heart Rate During Labor", American Academy of Family Physicians (1999).

Traditional fetal monitoring systems include are relatively bulky, expensive and intended to be used in designated centers (e.g., hospitals/physicians or offices). This arrangement raises several issues.

First, there exists a limited accessibility to fetal monitoring. Currently, in United States, pregnant mothers must commute to either a physician's office or a designated fetal monitoring center and these centers are often difficult for patients to access. This means that the pregnant mother should take a trip to the hospital for a monitoring session which puts the burden of time and expense both on the mother and accompanying person(s) as well as the healthcare system. Therefore, with traditional systems monitoring of pregnant mothers, who are not categorized as high risk, is limited to a few times during course of pregnancy. For example, typical testing is on the order of 2 times every week during the last trimester. This leads potentially to reduced efficacy of monitoring in terms of missing critical incidents. Immobility of the traditional system also means that pregnant mothers in remote areas and/or in the underserved areas with limited access to the healthcare system (e.g., in the case of many developing countries) are not being tested at all.

Second, there is limited mobility of the patient during fetal monitoring. Pregnant mothers who undergo fetal monitoring require a minimum of 45 minutes and up to 4 hours for each monitoring session. During this time the patient must remain in a relaxed position (usually recumbent) connected to the recording device. Putting on and adjusting the position of fetal monitoring system sensors takes substantial amount of time (i.e., on the order of 10-20 minutes). Using the traditional wired fetal monitoring system, in case that the patient needs to move during the test (e.g. goes to bathroom or the like) the setup needs to be removed and placed back afterwards. This adds additional time and cost burden in the hospitals.

Third, there is a lack of remote accessibility to data for evaluation. Currently most cardiotographic devices do not have the capability of digital storage and transfer. The usual manner in which a fetal monitoring study occurs involves a paper tracing that is carried to the health care provider or Physician for interpretation, and then stored in the patient's medical record. Often the length of these strips exceeds the capacity for storage for clinical, private physician practices and even hospital systems. Additionally, the lack of digital data transferability means that interpreting the data is possible in only places that trained care providers (i.e. nurses or physicians) are accessible.

Doppler ultrasound is a non-invasive monitoring approach to extract information about moving structures inside the body. It can be used for diagnosis of many cardiovascular conditions as well as in fetal health monitoring. Current ultrasonic technologies rely on bedside monitoring that is limited to the hospital and clinical settings. A major obstacle in transforming the traditional ultrasonic technologies into the emerging wireless health solutions is the significantly high computational complexity of the algorithms that process the plethora of the Doppler shifted data acquired from ultrasound transducers.

With the growing interest in wireless health technologies and their potential applications, efficient design and development of wearable medical devices is becoming unprecedentedly important to researchers in both academia and industry. See, e.g., R. Jafari, S. Ghiasi, and M. Sarrafzadeh, "Medical Embedded Systems," in *Embedded System Design: Topics, Techniques and Trends*, ser. IFIP Advances in Information and Communication Technology, A. Rettberg, M. Zanella, R. Düner, A. Gerstlauer, and F. Rammig, Eds. Springer Boston, 2007, vol. 231, pp. 441-444. The main driving factors in designing this new generation of the health paradigm include cost, power consumption, and wearablility, with power consumption being the center of many research efforts due to its dramatic influence on other design objectives. See, e.g., C. Park, P. Chou, Y. Bai, R. Matthews, and A. Hibbs, "An Ultra-wearable, Wireless, Low Power ECG Monitoring System," in *Biomedical Circuits and Systems Conference, 2006. BioCAS 2006. IEEE*, December 2006, pp. 241-244; P. Zappi, C. Lombriser, T. Stiefineier, E. Farella, D. Roggen, L. Benini, and G. Troster, "Activity Recognition From On-Body Sensors Accuracy-Power Trade-off By Dynamic Sensor Selection," *Lecture Notes in Computer Science*, vol. 4913, p. 17, 2008; V. Leonov, P. Fiorini, S. Sedky, T. Torfs, and C. Van Hoof, "Thermoelectric Mems Generators as a Power Supply for a Body Area Network," vol. 1, June 2005, pp. 291-294; S. Xiao, A. Dhamdhere, V. Sivaraman, and A. Burdett, "Transmission Power Control in Body Area Sensor Networks for Healthcare Monitoring," *IEEE Journal on Selected Areas in Communications*, vol. 27, no. 1, pp. 37-48, 2009; and H. Ghasemzadeh and R. Jafari, "A Greedy Buffer Allocation Algorithm for Power-Aware Communication in Body Sensor Networks," in *Proceedings of the eighth IEEE/ACM/IFIP International Conference on Hardware/Software Codesign and System Synthesis*, ser. CODES/ISSS '10. New York, N.Y., USA: ACM, 2010, pp. 195-204.

An important angle of low-power design is development of efficient signal processing and data reduction algorithms that reduce computation load of the processing units, allowing low-power low-cost processors to be embedded with the wearable device. While much work has been done on designing signal processing algorithms for a variety of sensing modalities such as motion sensors (H. Ghasemzadeh, V. Loseu, and R. Jafari, "Structural Action Recognition in Body Sensor Networks: Distributed Classification Based on String Matching," *IEEE Transactions on Information Technology in Biomedicine*, vol. 14, no. 2, pp. 425-435, 2010; A. Barth, M. Hanson, H. Powell, and J. Lach, "Tempo 3.1: A Body Area Sensor Network Platform for Continuous Movement Assessment," in *Wearable and Implantable Body Sensor Networks, 2009. BSN 2009. Sixth International Workshop on*, 2009, pp. 71-76.), Electrocardiography (D. Jun, X. Miao, Z. Hong-hai, and L. Wei-feng, "Wearable ECG Recognition and Monitor," in *Computer-Based Medical Systems, 2005. Proceedings. 18th IEEE Symposium on*, June 2005, pp. 413-418; M. Ayat, K. Assaleh, and H. Al-Nashash, "Prototype of a Standalone Fetal ECG Monitor," in *Industrial Electronics Applications (ISIEA), 2010 IEEE Symposium on*, 2010, pp. 617-622), and photo-plethysmogram sensors (J. Espina, T. Falck, J. Muehlsteff, and X. Aubert, "Wireless Body Sensor Network for Continuous Cuff-less Blood Pressure Monitoring," in *Medical Devices and Biosensors, 2006. 3rd IEEE/EMBS International Summer School on*, 2006, pp. 11-15), ultrasonic signal processing for stringent constrained computing platforms has not been studied in the past.

Traditional ultrasound technologies have been used in a variety of application domains such as ultrasound imaging (E. J. Gussenhoven, C. E. Essed, C. T. Lancée, F. Mastik, P. Frietman, F. C. van Egmond, J. Reiber, H. Bosch, H. van Urk, J. Roelandt, and N. Bom, "Arterial Wall Characteristics Determined by Intravascular Ultrasound Imaging: An in vitro Study," *Journal of the American College of Cardiology*, vol. 14, no. 4, pp. 947-952, 1989, ACC Anniversary Seminar) to produce pictures of the inside of the body, blood flow monitoring (A. Azhim, J. Yamaguchi, Y. Hirao, Y. Kinouchi, H. Yamaguchi, K. Yoshizaki, S. Ito, and M. Nomura, "Monitoring Carotid Blood Flow and ECG for Cardiovascular Disease in Elder Subjects," in *Engineering in Medicine and Biology Society, 2005. IEEE-EMBS 2005. 27th Annual International Conference of the*, 2005, pp. 5495-5498) to measure velocity of blood flow in different arteries for use in monitoring cardiovascular diseases, and Cardiotocography (C.-Y. Chen, J.-C. Chen, C. Yu, and C.-W. Lin, "A Comparative Study of a New Cardiotocography Analysis Program," in *Engineering in Medicine and Biology Society, 2009. EMBC 2009. Annual International Conference of the IEEE*, September 2009, pp. 2567-2570) to measure fetal heart rate and assess the effect of uterine contractions on fetal heart rate. However, the main challenge in transition from traditional ultrasound technologies to wearable platforms is the demand for a very high computational power. Compared to the other sensing modalities, ultrasound signals require a relatively high sampling frequency, producing large volumes of data that need to be processed. For instance, in a blood flow monitoring application, relevant information may appear in the frequency band of 100-4200 Hz, which may require a sampling frequency of 10 kHz as used in Azhim, et al, above. Moreover, a minimum sampling rate of 1600 Hz for capturing fetal movements is suggested in C.-Y. Chen, J.-C. Chen, C. Yu, and C.-W. Lin, "A Comparative Study of a New Cardiotocography Analysis Program," in *Engineering in Medicine and Biology Society, 2009. EMBC 2009. Annual International Conference of the IEEE*, September 2009, pp. 2567-2570. The large volume of sampled ultrasonic signals needs to undergo fast signal conditioning algorithms in order to extract relevant information in real-time.

As to patents, Rapoport, U.S. Pat. No. 5,257,627, discloses a portable apparatus for the non-invasive, simultaneous, self-testing of fetal and maternal signals. It includes a user display to indicate that the device is operational, an ultrasonic system to detect fetal heart rate connected to said device, a detection system for maternal input signal connected to said device, wherein the device has signal processor for simultaneously processing fetal heart rate and maternal input signals, and also has a communication linking means for the simultaneous transmission of fetal heart rate and maternal input data to a remote output device.

Lewis et al., U.S. Pat. No. 6,115,624, discloses an intrauterine catheter device for monitoring fetal and/or maternal heart rate, including an elongate housing having proximal and distal portions, an array of ECG electrodes on the distal portion and one or more acoustic or other mechanical sensors on the distal portion. A pressure transducer may also be provided on the distal portion. Processor circuitry compares the ECG signal with the output signal of the acoustic sensor to derive fetal and/or maternal heart rate. An intrauterine catheter device is also provided, including a reference electrode on its distal portion, and an array of active electrodes spaced apart from one another on the distal portion. The device may also include a pressure transducer on the distal portion and processor circuitry coupled to the array of active electrodes and/or to the reference electrode for deriving fetal ECG from signals produced by the array of active electrodes. Alternatively, the array of electrodes and acoustic sensors may be provided on a flexible pad that may be secured to the abdomen of a pregnant mother. An intrauterine catheter device is also provided, including a plurality of lumens communicating with a differential pressure transducer provided on its distal portion, and having a zeroing switch on its proximal portion for resetting the pressure transducer in situ.

Powell et al., U.S. Patent Application No. 2006/0149597, makes the following statements in the patent. It is said to provide a data processing tool for the viewing of real-time, critical patient data on remote and/or mobile devices. It is said that the tool renders graphical data on the screen of the remote device in a manner that makes it practical for the health care provider to accurately and timely review the data for the purpose of making an informed decision about the condition of the patient. Charting control is established and implemented using the latest GDI+, GAPI and PDA drawing techniques. The charting components provide landscape support, an ability to overlay patient data and patient images, zoom in/zoom out, custom variable speed scrolling, split screen support, and formatting control. It is said that the methodology operates as an asynchronous application, without sacrificing processing time in the mobile/handheld device. The methodology allows the critical patient data to be streamed in real-time to the handheld device while conserving enough CPU power to simultaneously allow the end user to interact at will with the responsive display application. The methodology is structured using object oriented concepts and design patterns. Each logical tier of the methodology, from the data access objects and the charting control objects, to the user interface objects, is structured with precise interfaces. The methodology implements an IT management console that allows system managers to monitor the exchange of data between hospital systems and the primary database, including all patient data packets, notifications and alerts, connected remote devices.

Hayes-Gill et al., U.S. Pat. No. 7,532,923, it discloses apparatus for detecting the heart rate of a fetus. The apparatus includes at least two detectors for detecting heart beats of the fetus, each detector comprising at least two electrodes for detecting ECG signals. A processor, which is coupled to the detectors, is used to process the ECG signals received from each detector and determine the heart rate of the fetus.

James et al., U.S. Patent Application No. 2007/0213672 discloses a monitor for fetal behavior by receiving ECG data from a set of electrodes attached to a material body. A waveform pre-processor identifies a succession of fetal ECG complex waveforms within the received data and a waveform processor determines differences in the processor succession of fetal ECG complex waveforms over time. An event logger determines from the determined differences a number of fetal movements during the period of time. Fetal spatial presentation and/or position within the uterus may also be determined from fetal ECG data acquired from a plurality of electrodes positioned on the maternal abdomen in a predetermined configuration. A number of fetal ECG complex waveforms are identified within the data, and each of the waveforms is compared with a set of predetermined fetal ECG complex templates ascribed to the predetermined electrode configuration to determine a template that best matches the identified fetal ECG waveforms.

Hayes-Gill et al., WO 2001/004147, it discloses a system for detecting uterine activity uses cutaneous electrodes on the maternal abdomen to obtain electrophysiological signals that can be used to obtain fetal and maternal heart rate. The apparatus includes a first input for receiving electrical signals from the cutaneous electrodes and a second input for receiving movement signals indicative of a movement of the maternal body from a movement detector. A signal processor separates a uterine electromyogram signal from fetal and maternal heart rate signals and filters out motion artifacts from the electromyogram using the movement signals. An output presents electrohysterogram (EHG) data from the uterine electromyogram signal.

Against this background is a compelling need to both bring healthcare to the underserved population, as well as to deliver more effective and cost effective healthcare. Further, there is a need to provide a marriage of wireless technologies in a way that are both safe and effective. Despite these compelling needs, the difficulty in detecting Fetal Distress Syndrome remains.

SUMMARY OF THE INVENTION

A wireless mobile wearable device is used to monitor the pregnant women uterine contractions and fetal heartbeat simultaneously. The device consists of a sensing component and a gateway for wireless communication with the data network. The instant wireless fetal monitoring system takes standard fetal monitoring technology augmented with wireless technology, to enable a new location independent paradigm of care. This device is used by a clinician or a skilled technician to monitor the patient (e.g., at a local clinic) while the diagnosis is performed by the clinician who is remote from the patient. Thus the device provides clinical expertise remotely, greatly benefiting patients especially in geographical regions that traditionally experience high rates of unattended pregnancies and poor fetal and maternal outcomes due to inadequate ante-partum care.

A wireless fetal and maternal monitoring system includes a fetal sensor unit adapted to receive signals indicative of a fetal heartbeat, or multiple fetal heartbeats in the case of multiple fetus, the sensor optionally utilizing a Doppler ultrasound sensor. A short-range transmission unit sends the signals indicative of fetal heartbeat to a gateway unit, either directly or via an auxiliary communications unit, in which case the electrical coupling between the short-range transmission unit and the auxiliary communications unit is via a wired connection. The short-range transmission unit is a low power transmission unit, preferably having specific absorption rate (SAR) of less than or equal to 0.1 watts/kg, and more preferably less than 0.05 watts/kg, and most preferably less than or equal to 0.01 watts/kg. The system includes a contraction actuator actuatable upon a maternal uterine contraction, which optionally is a EMG sensor. A gateway device provides for data visualization and data securitization. The gateway device provides for remote transmission of information through a data communication network. A server adapted to receive the information from the gateway device serves to store and process the data, and an interface system to permits remote patient monitoring.

The sensing component of the device includes sensors and short-range wireless interface and is worn by pregnant mother. The fetal heartbeat is detected using either ultrasound Doppler (detecting movement of fetus heart), sound microphones (detecting sound of fetus heart) or ECG sensors (detecting ECG of fetus heart). Contraction is measured either by a pressure sensor, EMG of uterine muscles or manually entered by user. The resulting signals are processed and transmitted out to the gateway, using short range wireless interface or a wired connection.

The data is visualized in the gateway for local monitoring then it is security encoded and sent out to a secure server using wireless internet connectivity (Wi-Fi, GPRS, Edge, 3G or the like) on the gateway. The contraction and heartbeat data are optionally reviewed by authorized users (care provider, relatives, or the like) over internet using a web access.

In yet another aspect of these inventions, signal processing and data reduction algorithms are provided which are computationally simple and enable real-time monitoring on lightweight embedded processors. In particular, algorithms that can efficiently measure fetal heart rate from Doppler shifted signals are used. An autocorrelation-based approach locates repeating patterns in the signal. An envelope detection technique is used to reduce the sampling rate in early stages of the processing, leaving only useful information for the more intensive computations in the autocorrelation stage. The algorithms are implemented and their effectiveness is demonstrated using a custom-designed hardware platform that is specifically designed for monitoring fetal heart rates.

In an effort to investigate efficient signal processing techniques for the ultrasound signals with a high computational demand, a signal processing model transforms sensor readings into useful information while reducing the amount of data passed through the processing chain as early as possible in the processing chain. While the inventions can be used in many application domains, the focus of the embodiments are fetal heart rate monitoring and an application where the algorithms are used for Cardiotocography.

In yet another aspect of these inventions, a wireless prenatal monitoring kit takes a unique wireless fetal/maternal monitoring device and combines with wireless biomarker devices into, preferably, a single kit which allows remote prenatal monitoring of high risk pregnant patients anywhere cell service or Wi-Fi is available. The wireless prenatal monitoring system is a unique pregnancy monitoring kit that combines wireless biomarker devices for monitoring fetal and maternal health information during the all phases, but particularly later, phases of pregnancy.

The wireless prenatal monitoring hub is a plug-in hub that optionally directly stores the data point at every time interval that the patient is monitored. The hub is used as a separate trending device to display the information for the mother throughout the day, month and throughout the pregnancy.

In the preferred embodiment, the wireless prenatal monitoring kit preferably contains the following: a wireless fetal maternal monitoring device, a wireless blood pressure device, a wireless glucometer, a urine reagent dip sticks, and a wireless communication device. The wireless communication device optionally may be a cell phone gateway or wireless hub.

The wireless prenatal monitoring kit is not limited to the specified devices. The prenatal monitoring kit can also include a pulse oxymeter or wireless weight scale. Any monitoring devices that are wireless, e.g., BLUETOOTH® driven, may be adapted for use in conjunction with the kit and system herein.

Accordingly, it is an object of these inventions to provide systems, methods and kits which can effectively deliver high quality health care, often remotely and wirelessly, at low cost, to provide clinically effective solutions.

BRIEF DESCRIPTION OF THE DRAWINGS

FIG. 10 is a connector and cable design for powering: (a) interconnection between two components; (b) interconnection between three components.

FIG. 11 is a typical baseband Doppler signals: (a) analog output from 100-500 Hz analog filter with 2400 samples per second ("sps") indicated; (b) output from digital envelope detector, before and after down-sampling to 240 sps.

FIG. 12 is an illustration of the data packet: (a) format; and (b) timing.

DETAILED DESCRIPTION OF THE INVENTION

Figure 1:
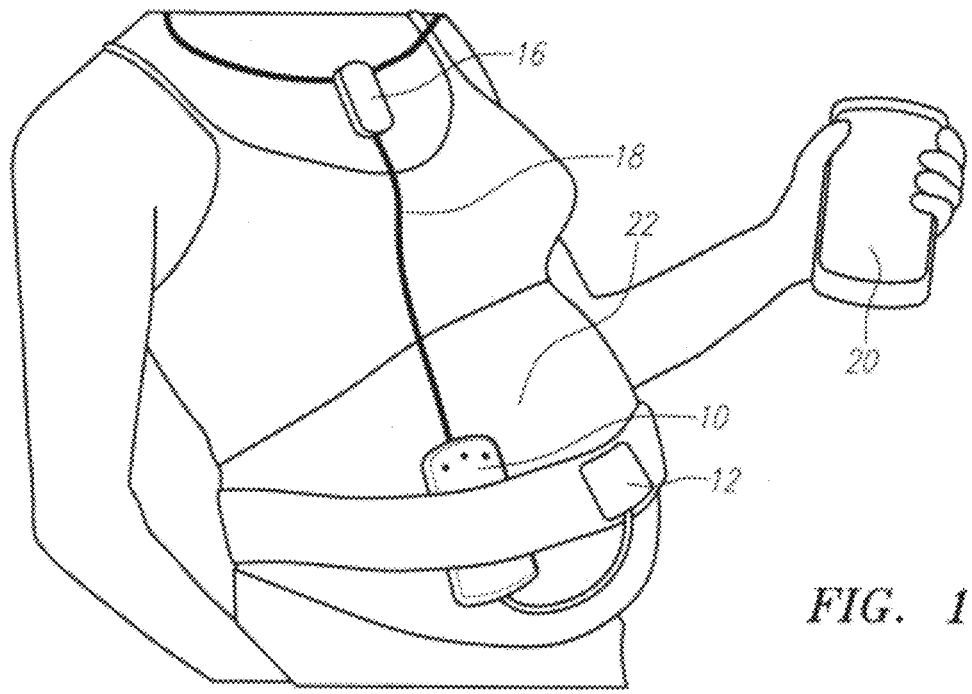
FIG. 1 is a perspective illustration of system components of the fetal monitoring system.

FIG. 1 illustrates one implementation of the wireless fetal monitoring system based on this invention. In one implementation, the device uses a fetal heartbeat detector, such as an ultrasound Doppler detector, and a pressure sensor, such as a toco transducer, for monitoring of contractions. The device consists of a central unit 10 which houses the fetal heartbeat detector (ultrasound piezoelectric transducer in one implementation of an ultrasound Doppler detector), operating at the frequency in the range of 1-10 MHz. The toco transducer 12 may be integrated with the sensor or central unit 10, or may be separate and connected to the central unit using a wire.

The central unit includes a short range communication module. A gateway 20 is used for local data storage, visualization and to communicate with the mobile data network to transmit data to the server. The short range communication is employed for safety considerations so that radio frequency (RF) emission with high power (that is required for communication to the cellular network) gateway 20 is placed relatively far from the mother/baby 22. The short range wireless communication module implemented in the central unit 10 has low power RF emission thus it is very less likely to be harmful. The short-range transmission unit is a low power transmission unit, preferably having specific absorption rate (SAR) of less than or equal to 0.1 watts/kg, and more preferably less than 0.05 watts/kg, and most preferably less than or equal to 0.01 watts/kg. This level of SAR is implemented as known to those skilled in the art, such as through the use of BLUETOOTH® technology. Preferably class 3 BLUETOOTH® technology or otherwise the lowest radiation class is utilized. Optionally, radiofrequency shielding is utilized.

One significant advantage of using a gateway in conjunction with the short range body sensor wireless link to the device against direct link from body worn sensor to mobile data network is reducing fetus and pregnant mother exposure to the RF radiation of wireless fetal monitor.

Both wireless gateway and BLUETOOTH® module emit non-ionizing radiation at frequencies ranging in 1-2.5 GHz. The FCC limit on the Specific Absorption Rate (SAR), a measure of the rate of energy absorption by the body when exposed to an RF field (see, e.g., C. K. Choul, et al, "Radio Frequency Electromagnetic Exposure: Tutorial Review on Experimental Dosiinetry", Bioelectro-magnetics, Vol. 17, Issue 3, pages 195-208 (1996)), for cellular telephones is 1.6 W/kg.

The SAR rate of the gateway is comparable to typical smart phones, in the range of 0.5-1.5 W/kg (see, e.g., Electromagnetic Fields and Public Health: Mobile Phones", World Health Organization, Fact Sheet No 193, May 2010) A BLUETOOTH® radio module configured in class II generates a SAR level of ~0.01 W/kg. Therefore, by utilizing a gateway, placed relatively far from the pregnant woman the SAR level can be reduced by two orders-of-magnitude and well below FCC standards. Using the optional external BLUETOOTH® necklace, rather than the built-in module, further diminishes the undesired RF emission exposure to the fetus to an even less significant value.

In order to eliminate any concern regarding absorption of radio frequency signals by the fetus, an auxiliary communication unit 16 is optionally utilized. In one variation, the auxiliary communication unit is in the form of a necklace, which locates the transmitter to the gateway 20 at a significant distance, such as at least two feet (though this distance will vary based on the height and physical structure of the mother) from the fetus. In this implementation, the communication from the central unit 10 to the auxiliary communication unit 16 may be wireless, but is preferably wired via connection 18. The wired, i.e., not wireless, communication from the central unit 10 minimizes radiation to the fetus.

FIG. 1 illustrates the form factor implementation for the different components of the sensing front-end. The central unit integrates the ultrasound transducers, processing and control circuitry, and the internal BLUETOOTH® communication module.

Separate belts are preferably used to hold the central unit and toco sensor so that during operation, position of sensors can be independently optimized. The central unit includes ultrasound transducers as well as control, processing and BLUETOOTH® communication circuitry. A toco pressure sensor, an optional audio feedback earphone and the optional external BLUETOOTH® necklace can be plugged in to the central unit.

Figure 2:
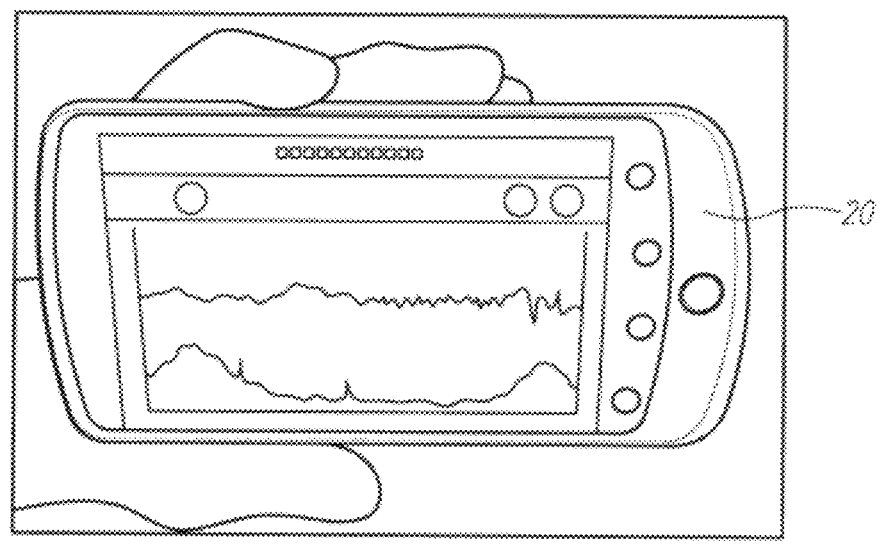
FIG. 2 is a perspective view of a gateway device displaying a fetal or maternal images.

FIG. 2 is a plan view of a representative gateway device 20. The gateway device may preferably include data visualization. In FIG. 2, the fetal heartbeat is shown in the upper waveform, and the signal corresponding to the maternal contractions are displayed in the lower portion. Optionally, the display may comprise a touch screen display. The gateway device further preferably includes encoding functionality, to permit the secure transmission of medical data.

Figure 3:
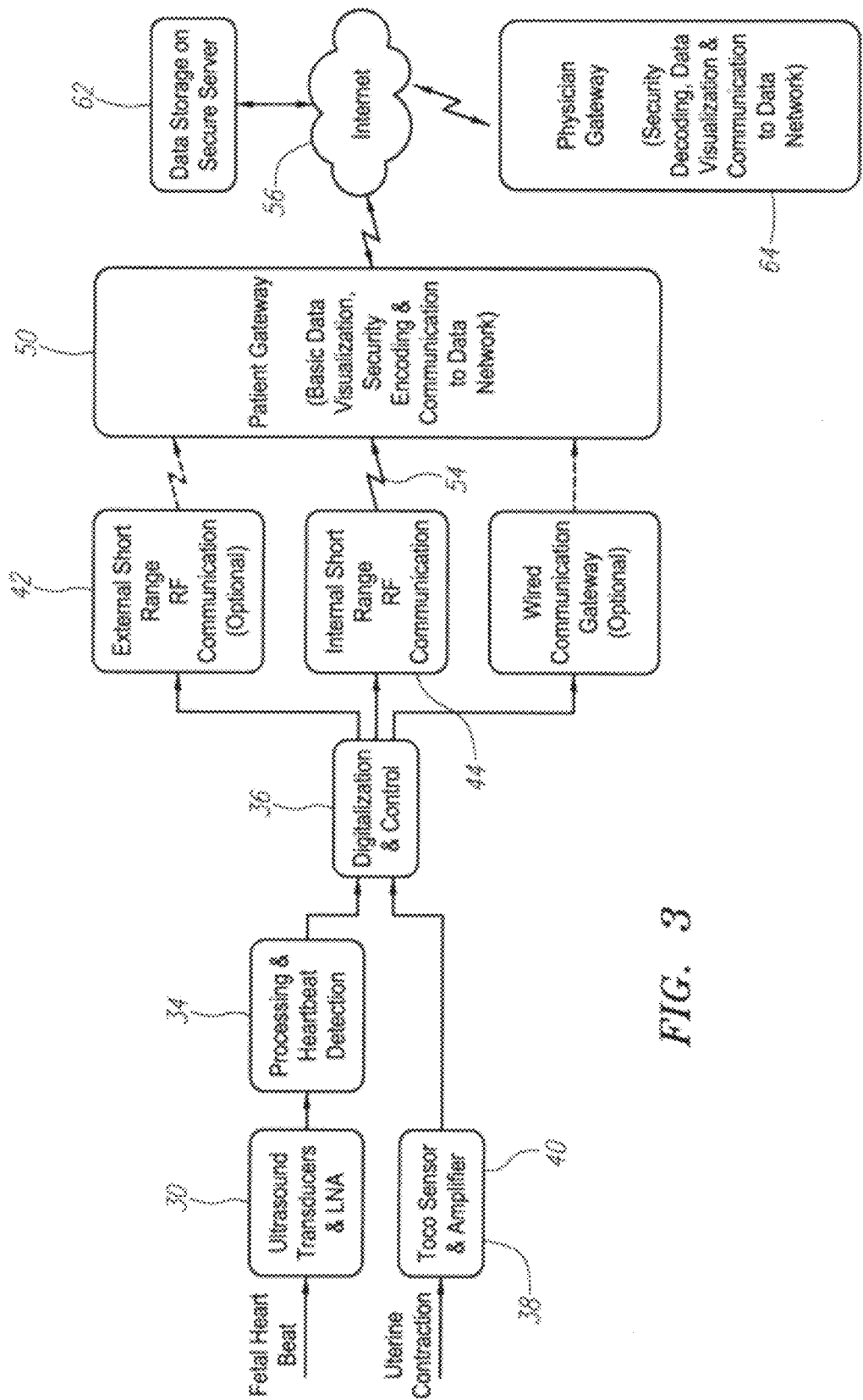
FIG. 3 is a functional block diagram of the system for fetal and material monitoring.

FIG. 3 shows a schematic functional block diagram of one implementation of the system. One possible architecture for the system comprises a wireless sensing interface, data transmission gateway, data storage, and user interface over the interne. The fetal heartbeat detector, such as a piezoelectric ultrasound transducer 30, is an input to the sensing hardware 32. The sensing hardware 32 may be characterized as wireless, though certain embodiments contemplate wired connections. The sensing hardware 32 may optionally include an amplifier, such as a low noise amplifier (LNA). The output of the sensor 30 is provided to signal processor 34, such as Doppler signal processing detector, for processing and heartbeat detection. In turn, the signal digitization unit 36 digitizes the signal, such as through an analog to digital converter (ADC), and may optionally perform heart rate calculation, as well as to provide control and data functions. The maternal uterine contraction actuator, such as a toco pressure sensor 38, provides output corresponding to maternal contractions to amplification and signal conditioning circuit 40, again optionally a utilizing a low noise amplifier (LNA), which in turn is passed to the signal digitization unit 36. In one embodiment, an internal short range transmission unit 42 is provided which communicates with the gateway 50. Alternately (or in combination) the external short range transmission unit 44 communicates, such as by RF communication, with the gateway 50. In the later embodiment, preferably a wired communication path 54 is provided. A communication network 56, such as the internet or telephone network, couples the device to a server 62, preferably a secure data server. A user interface 64 optionally permits remote patient monitoring, preferably in a graphical format. The user interface 64 may be displayed on a computer or other web-enabled device.

Figure 4:
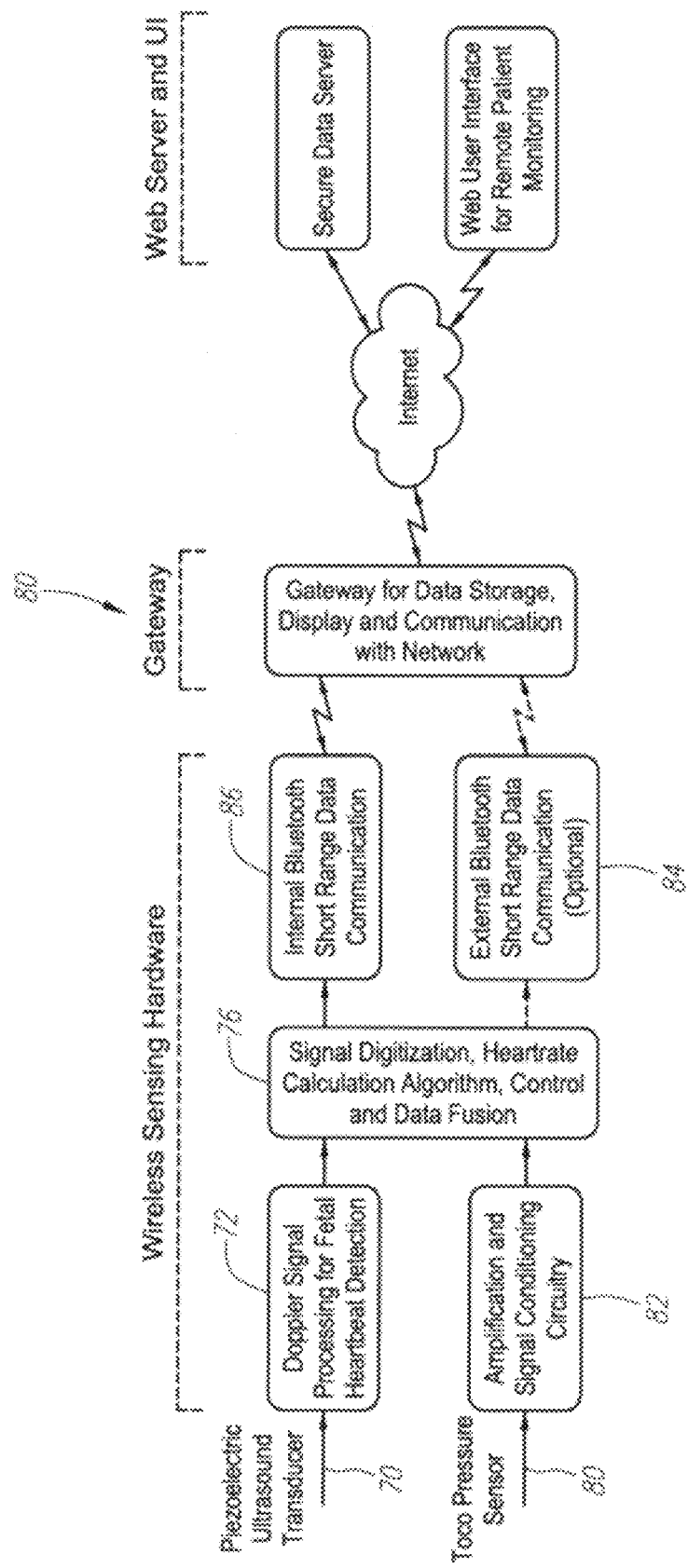
FIG. 4 is a second functional block diagram of the system for fetal and material monitoring.

FIG. 4 shows a schematic functional block diagram of one implementation of the system. The fetal heart beat 70 is received by the sensor 72, shown in FIG. 4 with the ultrasound embodiment being a transducer and optional amplifier, most preferably a low noise amplifier. The output of the sensor 72 is communicated to the processor 74, preferably for signal processing and heartbeat detection. Uterine contraction information 80 is detected via sensor 82, shown in this implementation as toco sensor and amplifier 82. Optionally, the sensor 82 includes amplification and signal conditioning circuitry. The output of the processor 74 and sensor 82 is managed by digitization and control block 76. Optionally, the control block 76 includes one or more of the functions of signal digitization, heart rate calculation systems or algorithms and data fusion. The output of block 76 is communicated to gateway 80, which preferably serves as a gateway for data storage, display and communications with the network. Various communication path options include external short range RF communication path 84, such as BLUETOOTH®, and internal short range RF communication path 86, such as internal Blutooth short range data communication, and wired communication 88 to the gateway 80. The wireless communication paths are low power communications. The short-range communications preferably have specific absorption rate (SAR) of less than or equal to 0.1 watts/kg, and more preferably less than 0.05 watts/kg, and most preferably less than or equal to 0.01 watts/kg. A communication network 90, such as the interact, couples the gateway 80 to storage 90, preferably secure server based storage, and an optional physician gateway 94 or other user interface, preferably for security decoding, data visualization and communication functions.

One particular implementation of the sensing hardware is described with reference to FIGS. 3 and 4. Front-end of the system includes an ultrasound Doppler heartbeat detector and a toco pressure sensor, resembling a standard fetal monitoring system. A set of two half disc 2 MHz PZ-27 ultrasound ceramic transducers (Ferroperm, Piezoceramics) along with off-the-shelf electronics are employed to detect fetal heartbeat, and to provide an audio feedback to help positioning of the ultrasound device during monitoring. A low-cost 8-bit microcontroller (PIC16F688, Microchip) is used for system control, analog to digital conversion via an on-chip10-bit ADC, onboard signal processing and communication with the BLUETOOTH® module.

Due to motion artifacts and/or inappropriate positioning of transducers on a mothers abdomen, the heartbeat detector often misses one or more heartbeats. An algorithm for heartbeat to heart rate conversion, embedded on microcontroller, eliminates the erroneous measure via comparing input beat period with the previously stored value. In case that current reading is outside of ±25% of the stored value, the algorithm drops the new reading and raises a flag. If 6 consecutive readings are constantly out of that range the new reading is stored as updated measurement result.

A low-cost disposable toco sensor (FeatherLiteToco, Ventrex) which consists of a pressure transducer configured in a Wheatstone bridge is used for contraction monitoring. An instrumentation amplifier with a gain of 100 amplifies the signal to the ADC input range. Further baseline subtraction and gain adjustment is implemented in the gateway software. The device makes an authenticated link with the gateway using a BLUETOOTH® module (RN-41, Roving Networks) configured in Serial Port Profile. The module's output RF power can be programmed for either class I, II or III. An optional external BLUETOOTH®, in a necklace form factor is designed so when it is plugged in to the unit, substitutes the internal BLUETOOTH®.

Current consumption of the module is dominated by electronics driving ultrasound crystals and the BLUETOOTH® module, measured at 60 mA and 25 mA, respectively from the 3.3V regulated supply. The device is powered by two standard AAA batteries which results in approximately 8 hours of constant running time. By powering from separate up-converting voltage regulators, interference between the sensing interface electronics and the BLUETOOTH® module is minimized.

Figure 5:
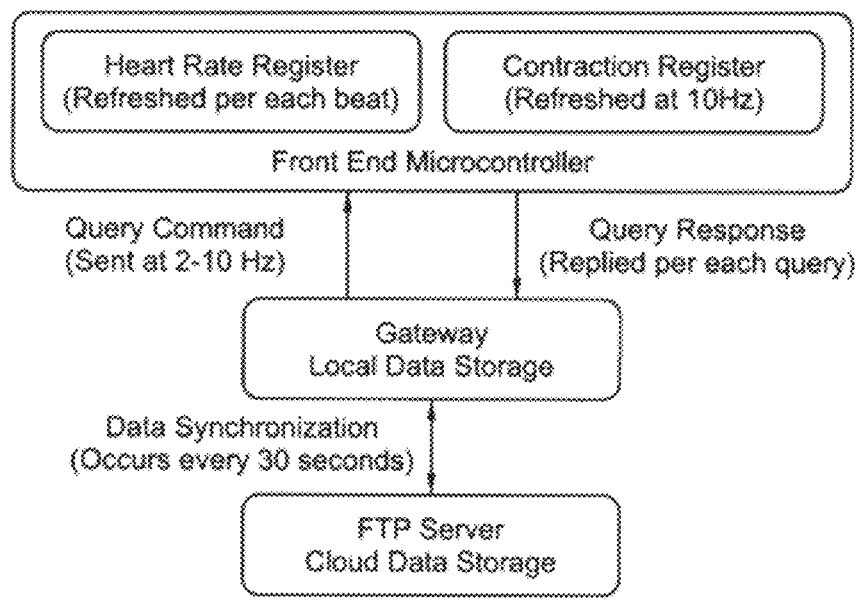
FIG. 5 is a schematic diagram showing timing of data transmission in the system.
Figure 6:
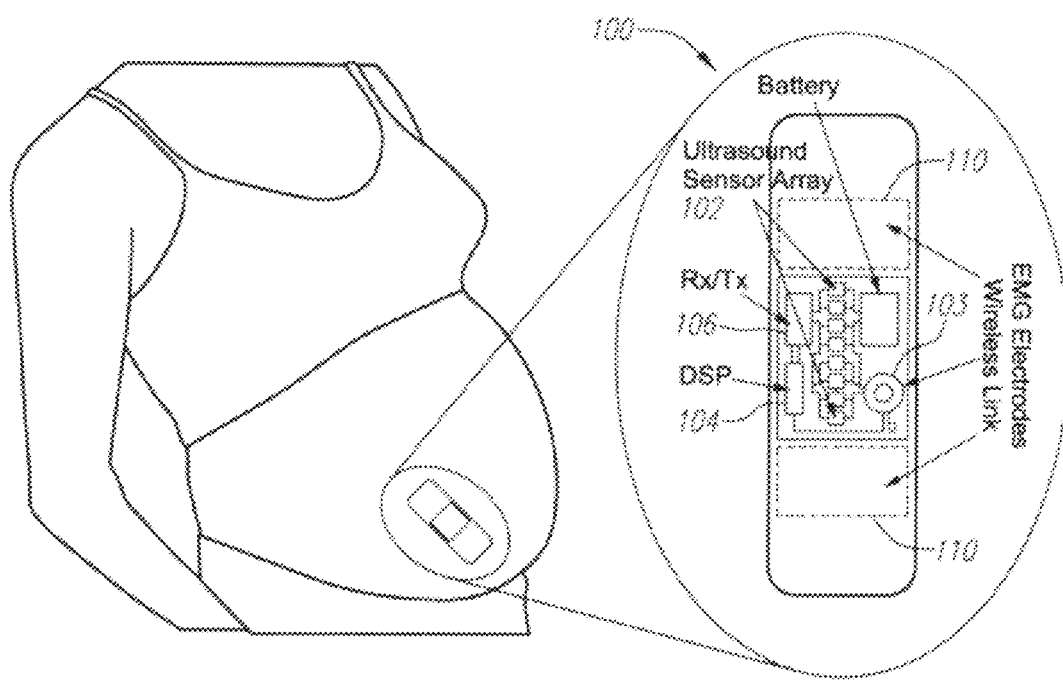
FIG. 6 is an illustration of patch for fetal monitoring system.

FIG. 5 depicts various timings for data transmission in the system. The decision as to what data to send within the system, and how frequently to send it, strongly relate to the power consumption of the system. Internal hardware registers for heart rate and contraction are being updated each beat and at a 10 Hz rate, respectively. A transmission between the gateway and the central unit is initiated by the gateway and acknowledged by a 3 byte response from the central unit consisting of the heart rate, contraction information, and an error code at an update rate of 2-10 Hz. Data synchronization in this embodiment occurs at a lower frequency than above, such as every 30 seconds. The gateway has been implemented as an application on an Android based Smartphone (Nexus One, Google/HTC). It uses internal BLUETOOTH® on the phone to create the link with the sensing hardware and chooses the best available data communication channel to the network in between Wi-Fi, GPRS, Edge or 3G. The gateway operatively communicates with storage, preferably cloud data storage, and may include File Transfer Protocol (FTP) server cloud data storage. Cloud computing in all of its forms may also be used for achieving the functionality of the systems and methods described herein. (See also the description of cloud computing in connection with FIG. 23, which discussion applies generally throughout this specification FIG. 6 depicts a patch 100 based implementation of the fetal and maternal monitoring system. This system implements the sensing part invention in on a patch (adhesive bandage) format. In this implementation one single pair, or an array of, ultrasound transducers 102 is employed for heartbeat detection and monitoring of electrical activity of uterus mussels (i.e. uterus EMG) is used for uterine contraction detection. This technique eliminates the need for toco sensor and the belt. A two or three lead EMG recording system is implemented in the patch and placed on the mother's belly. The recorded signal includes mother's ECG, EMG of uterus mussels and Fetal ECG (FECG).

The EMG signals occupies a different band in frequency and could be filtered out from other signals and used for tracking uterine contractions. The ultrasound transducers preferably are arranged as an array that enables the electronics process the signal to minimize the need to repositioning of the patch due to baby movements. This arrangement is described in co-pending U.S. Provisional Patent Application Ser. No. 61/327,975, entitled "Ultrasound Patch", filed Apr. 26, 2010, incorporated herein by reference as if fully set forth herein.

FIG. 6 shows the detail of utilizing a linear array of miniaturized ultrasound transducers built into an adhesive patch for monitoring a fetal heartbeat. A linear array of 2 or 4 or 8 transducer elements 102 (e.g., Lead Zirconate Titanate (PZT)) is used to sweep the targeted area with ultrasound waves. The penetration depth is dependent on the frequency of the signal. For fetal heartbeat monitoring, a higher frequency signal (about 2 MHz-10 MHz) is used, as it needs to penetrate deeper into the body, resulting in much more signal attenuation. Such an ultrasound patch can be utilized in a variety of applications depending on the required power, configuration, size and characteristics of the ultrasound transducers, which in turn dictate the depth of the ultrasound signal penetration, detection sensitivity and resolution, and system complexity. Optionally a signal processor 104, preferably a digital signal processor (DSP) is used to analyze and process the data from the array. Communication module 106 provides communication, including at least transmission, but preferably also reception. Communication is preferably through the wireless link 108. A pair of EMG electrodes 110 are preferably disposed adjacent the electronics components.

In a Doppler ultrasound, the measured shift in the frequency/phase of the received signal in comparison to the transmitted signal is of interest, even though it may be very small. This method is called continuous-wave (CW) Doppler, where the change in frequency and phase of the reflected ultrasound signal is measured. This technique is different from the traditional sonographic techniques and does not be used to create an image, but rather to measure the fetal heart rate, and optionally other parameters such as flow in blood vessels, veins, and arteries.

Control circuitry is coupled to the transmission system and the receiver system. The control system may include analytical or analysis functions. A processor may be provided, either within the patch, or external to the patch, to perform analytical or analysis functions.

In this patch embodiment, in addition to sensors for fetal heartbeat monitoring, dry electrodes are provided to record bio-potentials such as electromyogram (EMG). FIG. 6 shows a configuration for a multi-purpose adhesive patch, integrating both microphones and ultrasound transducers in a wearable patch. The top view of the patch is the side that faces the user and depending on the needed functionality, the user can turn the device On/Off and select between the modes: auscultation of sounds of the body or listening to the heartbeat. Temperature sensors and accelerometers are among other possibilities, e.g., in a wearable, adhesive patch, one or more accelerometers can additionally capture the activity level of the person to help in additional assessment of health and well being. Additional ultra-miniature and low-cost sensors or electrodes into the platform for expanded diagnostic capabilities. For example, microphones to hear other body sounds, such as lung sound or maternal heartbeat.

In one implementation of the patch, the wearable patch for use on a body is in the form of a planar pad. The preferred dimensions of the patch are 80 mm×25 mm and thickness 5 mm or less, and most preferably 60 mm×20 mm 3.5 mm or less. The patch should be light-weight, about 16 grams or preferably weighing 8 grams or less.

Figure 7A:
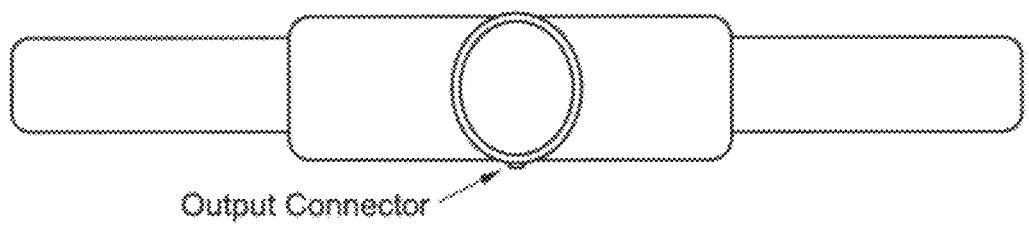
FIG. 7 components of the fetal monitoring device: (a) Toco sensor with belt; (b) FHR monitor.
Figure 7B:
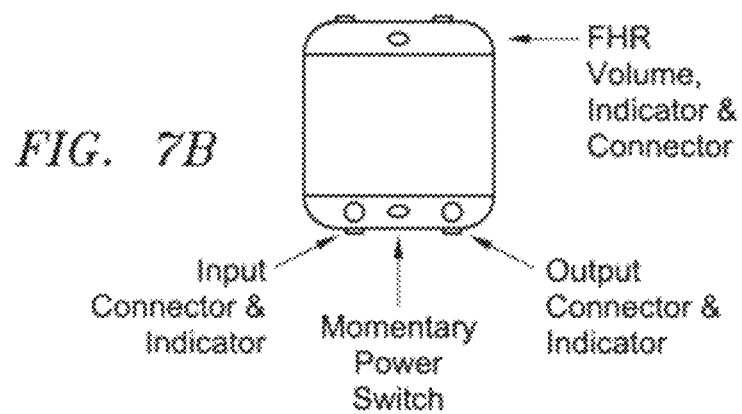

The following detailed description has applicability to systems for multiple births, but also has general applicability for systems and methods for single births. The fetal monitoring device consists of two components, illustrated in FIG. 7, which can be assembled in a variety of ways. The components are (a) a passive strain gage ("toco" sensor) used for contraction monitoring; and (b) a Fetal Heart Rate (FHR) monitor based on continuous-wave (CW) Doppler ultrasound. The FHR monitor includes analog signal processing for both sensor modalities, a BLUETOOTH® transceiver, and a low-cost microcontroller, which provides digital signal processing (DSP) and system control, 8 bit analog-to-digital conversion, and communication with the BLUETOOTH® transceiver. A second, identical FHR monitor can be included as illustrated in FIG. 8 to monitor the FHR of a twin, or for use as an external (off-body) BLUETOOTH® transceiver, since by design the internal BLUETOOTH® transceiver of an FHR monitor is disabled when another FHR monitor is connected to its output.

Data is passed serially from the first (nearest toco) monitor in the daisy chain to the last. In all configurations, data is transmitted from the last FHR monitor in the chain to a nearby cellular gateway using a BLUETOOTH® communication module. In addition to the nominal (c) and twin (d) configurations shown in the figure, the FHR monitor may be used stand-alone (without toco sensor), or a 3rd FHR monitor may be connected at the end of the chain to be used as an off-body transmitter for a twin configuration.

Figure 8:
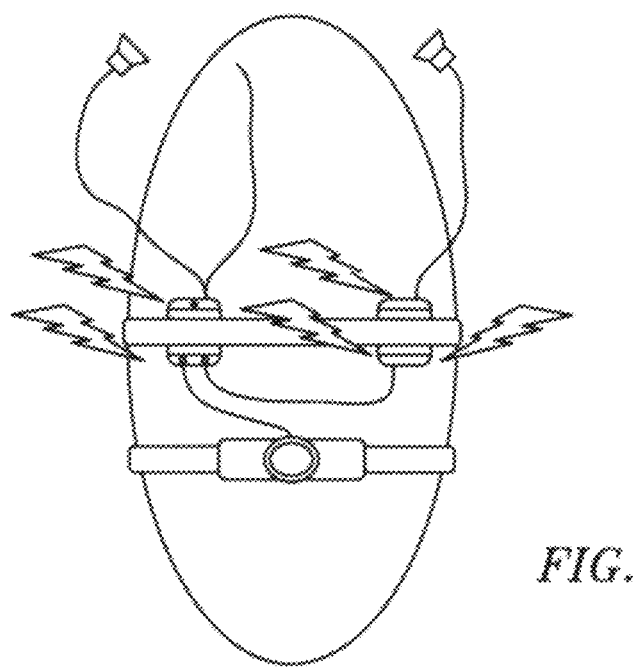
FIG. 8 is plan view illustrating placement of the fetal monitoring system on the mother.

When fitted on the mother, the device would appear approximately as shown in FIG. 8. The architecture employed in the design of this fetal monitoring device could support any number of births, but it may be impractical to fit the monitor for more than twin births. By providing twin FHR monitors, the monitoring time of a mother can be cut in half.

The device has been developed with usability in mind. The user must simply plug in components in order to activate power and data collection. The FHR monitor automatically detects the presence or lack of a connection, and its type. LED indicators illuminate to inform the user of the monitor status: green for a valid input connection, blue to signify that the BLUETOOTH® transmitter is operating, and flashing amber for the heartbeat.

Additional features simplify the fitting procedure. When the toco belt is tightened, the green indicator flashes to signify that contraction threshold has been exceeded, and ceases to flash when the belt is loosened to produce strain below a slightly lower threshold. Also, the demodulated analog output from the Doppler signal processing employed by the FHR monitor is buffered and provided to a stereo audio jack so both mother and practitioner can listen to the sound of the heartbeat during fitting.

To prevent data loss in the event that communication is lost during a monitoring session, the FHR monitor includes a back-up memory, by way of example a 4.5-hour backup memory, which can be implemented using a 1-Mbit serial EEPROM that is written and read using a SPI interface running at 1.5 Mbps. When the memory backup feature is enabled, each data packet that is transmitted to the serial daisy chain or to the BLUETOOTH® transceiver, is also written to the EEPROM.

The backup memory is set up via the cellular gateway. During memory setup, the blue light flashes to indicate that data collection is suspended. A simple command language has devised in which an initial receipt of "M" by the BLUETOOTH® module switches operation from normal (acquisition) mode to memory mode, in which received characters are processed as commands to enable/disable memory backup, to set the memory address, and to upload data from the memory.

Figure 9:
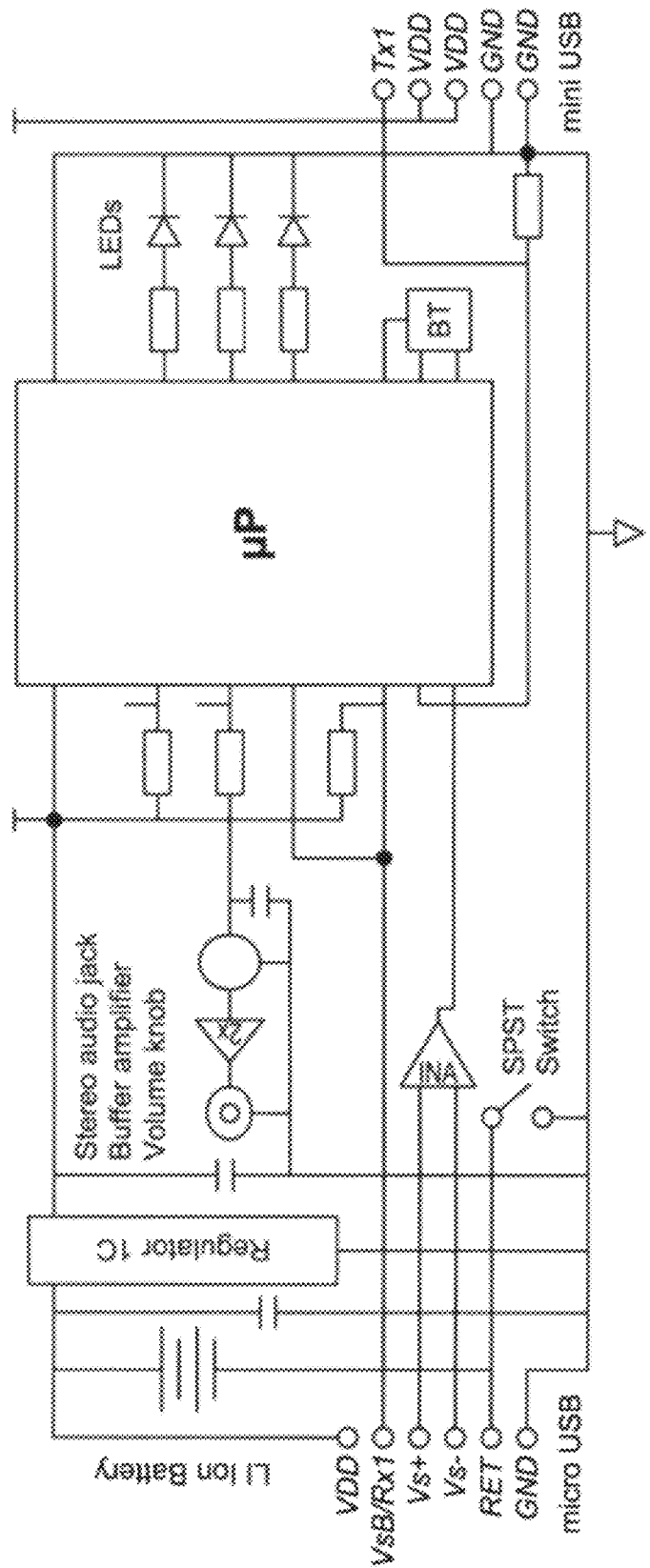
FIG. 9 is a simplified schematic of the FHR user interface.

As to possible circuit design, the FHR monitor is controlled using a low-cost, 8-bit microcontroller that includes all the analog-to-digital conversion, timing, and indicator drive required by the monitor, as illustrated in FIG. 9. The device is powered using an 850-mAHr rechargeable Li-polymer cell, and includes two linear 3.3-V regulators to provide one stable power supply voltage to the BLUETOOTH® transceiver, and a second stable supply voltage to all other circuits. Power is activated when a momentary SPST switch is closed and held, or when a device is plugged into its input connector, as described below. The practitioner may mark events using a second SPST switch in the form of a squeeze ball, e.g., that momentarily grounds pin A5 in the simplified schematic.

A piezoresistive Wheatstone bridge toco sensor is connected between the VsB and RET pins of the input connector, with its differential sensor output connected to the Vs+/Vs− pins. Alternatively, an FHR monitor may be connected to the input port, in which case the serial data output Tx1 connects to the serial data input Rx1, and the supply voltage VDD is used to bias the INA inputs.

As illustrated in FIG. 10, components may use a mini-USB connector for output, and micro-USB for input, to prohibit connection from input to input, or output to output. Data communication, whether it be analog toco or serial digital, is accomplished using the 4 wires of a USB cable, while powering is accomplished using the cable shield as a 5th connection. A jumper on the output connector between the shield and battery return line is used to close the circuit and power the FHR monitor when the cable is correctly inserted into both connectors.

Upon start-up, the FHR monitor must determine what type of device is connected to its input port, i.e., a toco sensor, an FHR monitor, or a simple powering plug with no associated sensing device. This is accomplished through a combination of pull-up and pull-down resistors of the appropriate ratios (not shown), in addition to logic in the firmware of the embedded microprocessor. As was shown in FIG. 9, one signal pin of the input connector serves as either sensor bias (VsB) or serial data receive (Rx1), depending on the type of device that is connected. The FHR monitor includes a pull-up resistor which makes this signal a constant high when no device is connected to this pin. When a toco sensor is connected, however, the 10× lower resistance of the toco sensor pulls this logic level to a constant low. When an FHR monitor is connected to the input connector of a twin monitor, the activity of its serial data output can be detected to reveal this third connection type.

There are only two types of output connections that he detected, i.e., a twin FHR monitor or no connection. This is accomplished by providing a pull-down resistor on the serial data transmit line (Tx1). If no device is connected to the output connector, the logic level is pulled low. When an FHR monitor is plugged into the output connector, the pull-up resistor on its Rx input, having a 10× smaller value, results in a high logic level. Since output connections may be made or broken after start-up, this connection must be tested each time data is to be transmitted. If an FHR monitor is detected, the internal BLUETOOTH® module is disabled and data is sent to the serial daisy chain. If no connection is sensed, the data is sent to the BLUETOOTH® transmitter.

For audio signal processing, the device preferably uses a precision 2.0-MHz sinusoid is derived from the 12-MHz master clock, and buffered to drive the transmitting ultrasonic transducer. The signal from the receiving transducer is first amplified using a tuned, JFET common-source amplifier, then demodulated using a chopping mixer. The baseband signal is then passed through a four-stage band-pass amplifier that passes the Doppler-shifted signal in the frequency range of 100-500 Hz. This audio signal is amplified using a PGA and input to the ADCs, and is also buffered to drive a stereo ear-piece. The total voltage gain may be varied from 64 dB to 106 dB.

The differential input from the toco sensor is simply amplified by 46 dB using an instrumentation amplifier (INA), then input to its ADC and averaged over 120 samples (a half second) in the microprocessor. Additional baseline subtraction and gain adjustment is implemented in the gateway software, and as part of the fitting calibration procedure.

For digital signal processing, the FHR is calculated using a robust algorithm that is based on autocorrelation, described in more detail, below. Given the requirement of a minimum FHR of 30 beats per minute (BPM), the autocorrelation window must be 2 seconds in duration. A preliminary examination of typical Doppler signals revealed that the 100-500 Hz signal (FIG. 11 top) could be sampled at a rate as low as 2400 sps to capture the envelope of baseband Doppler signal to an accuracy of 92%. This examination further revealed that the digitized envelope could be down-sampled to rate of 240 sps (FIG. 11 middle) while maintaining an accuracy of 96% in peak amplitude. Based on this sample rate and the requirement of 2-second autocorrelation window, the processor is required to compute single-instruction multiplications, additions, and memory transfers at a rate of about 1.5 MIPS using a RAM size of 4 kbytes. The FHR calculation is completed by analysis of the autocorrelation data, which must be updated at least twice per second, and this increases the total processor speed requirement to less than 3.0 MIPS.

As to data format and daisy chain communication, the serial data chain could be extended indefinitely. The digital signals that originate with the first FHR monitor in the chain, i.e. the "primary", are transmitted serially using RS-232 format. The toco sample would be dropped into the beginning of a data packet, and the value 0 could be used as a marker to indicate that the toco sensor is not present, as in stand-alone FHR monitoring. The primary FHR monitor would drop its FHR data into the next slot and marks all other slots in the packet as empty. Any additional FHR monitors in the chain would recognize that they are not the primary and would instead drop their FUR data into the first empty slot, then pass it up the chain. The final FHR monitor in the chain would transmit the data using its BLUETOOTH® module.

While the concept could be extended indefinitely, it is limited by the chosen packet size. In the present implementation, illustrated in FIG. 12, the data packet includes four bytes, in which the first byte synch is used for synchronization and event marking, the 2nd byte is used for toco data, and the 3rd/4th bytes are used for FHR data from the primary/twin FHR monitors. The LSB of the synch byte is used for event marking and all other bits are high, so it has an integer value from 254 to 255 and can be differentiated from the toco and FHR data bytes. The toco byte has a minimum value of 1 (no abdominal strain) and a maximum value of 253 (maximum abdominal strain), since 0 is reserved to indicate that the toco sensor is not present. The FHR data bytes have units of BPM, and the circuitry is designed for a range of 30 to 240 BPM. Codes of 0 and 253 are used to represent "unit not present" and "heartbeat not detected," respectively.

Including start and stop bits, a data packet consists of 40 bits, which is transmitted in 16.7 msec at 2400 bps. When the BLUETOOTH® module is enabled, data is transmitted wirelessly upon a query ("Q") received from the module. When the wireless module is disabled, data is sent to the daisy chain Tx1 following each packed received from Rx1, or at regular update intervals (each half second in the current implementation). Since a twin FHR monitor could be connected/disconnected to/from Tx1 at any time after startup-up, the device is programmed to test the output connection before transmission of each data packet, which requires that the serial port circuits be temporarily disabled, then re-enabled prior to transmission.

Figure 13:
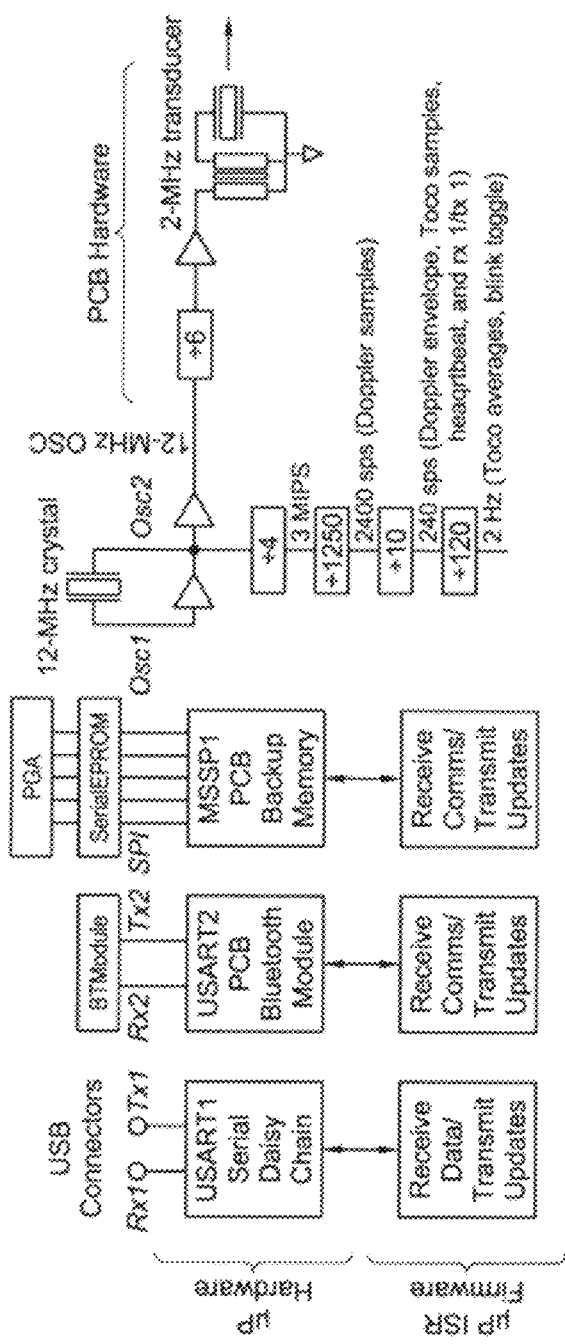
FIG. 13 is a block diagram of the signal processor with timing generation.

As illustrated in FIG. 13, in one implementation of the system, all timing signals may be derived from a 12-MHz crystal oscillator. This precision master clock is divided by 6 using a Johnson counter to produce the 2-MHz drive required by the ultrasonic transducer. It is also divided using counters in the microcontroller hardware/firmware to produce a 3-MIPS instruction clock; 2400-sps sampling clock for the demodulated Doppler signal employed by the FHR monitor; 240-sps clock used to down-sample the Doppler envelope, acquire toco samples, flash the heartbeat indicator LED, and receive/transmit serial data bytes; and, 2-Hz clock to trigger output updates and toggle blinking indicators.

Figure 14:
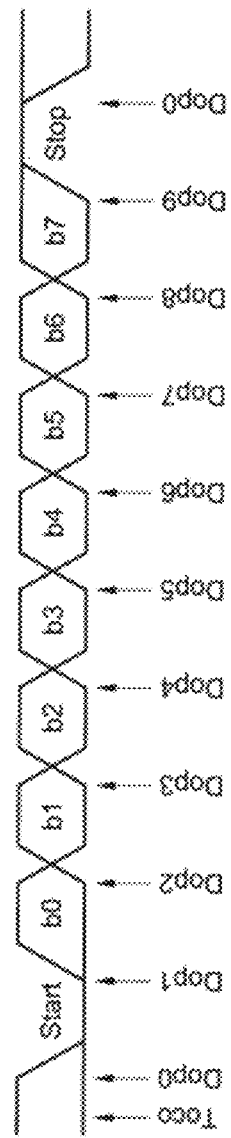
FIG. 14 is an illustration of synchronous communication and sample timing.

By ensuring synchronicity of timing between ADC samples and serial communication, interference from the communications circuitry can be minimized, as illustrated in FIG. 14. Just prior to transmission of each data byte, a toco sample is taken. Just prior to each bit transition in the serial stream, a Doppler sample is taken. As such, a disturbance introduced by the serial communication circuitry has a full bit period, about 417 μsec, to settle prior to sampling.

Figure 15A:
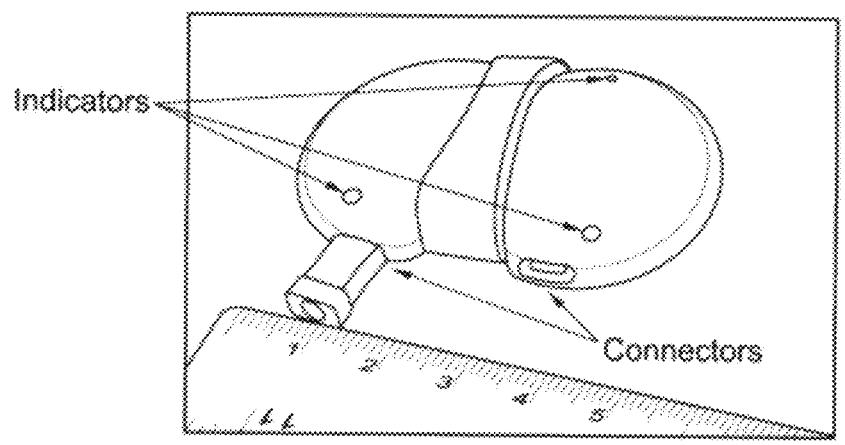
FIG. 15 shows photographs of system components: (a) assembled FHR monitor, and (b) toco sensor.
Figure 15B:
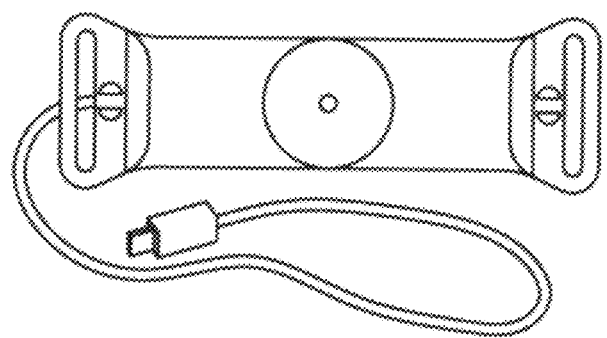

Circuits may be fabricated on a printed circuit board (PCB) having dimension 115.5 mm by 95.0 mm, for ease of debug and test, then laid out for the final size and form factor, a double-side, oval PCB having dimensions 85.4 mm by 66.6 mm, of which 1480 mm2 are occupied by the rechargeable, lithium-polymer battery. Photographs of the assembled device components are provided in FIG. 15. Sub-figure (a) shows the assembled FHR monitor, which is 97.5 mm×72 mm×20 mm at widest points, excluding the belt clip, and has a mass of just 85 grams (3 oz.). The toco sensor is pictured in sub-figure (b).

The test results were obtained using the assembled FHR monitor when possible, and from the PCB with increased form factor, when necessary. The schematic designs of the circuitry are equivalent in the two versions. Wireless sensor data was captured using the BLUETOOTH® transceiver of a laptop computer.

Total measured current draw from the rechargeable, 4.2-V lithium-polymer battery is 112 mA, where 60 mA is drawn by the BLUETOOTH® module, and 13 mA is drawn by the transducer drive circuitry. The unit may therefore operate for almost 8 hrs before recharging the 850-mA battery.

Figure 16:
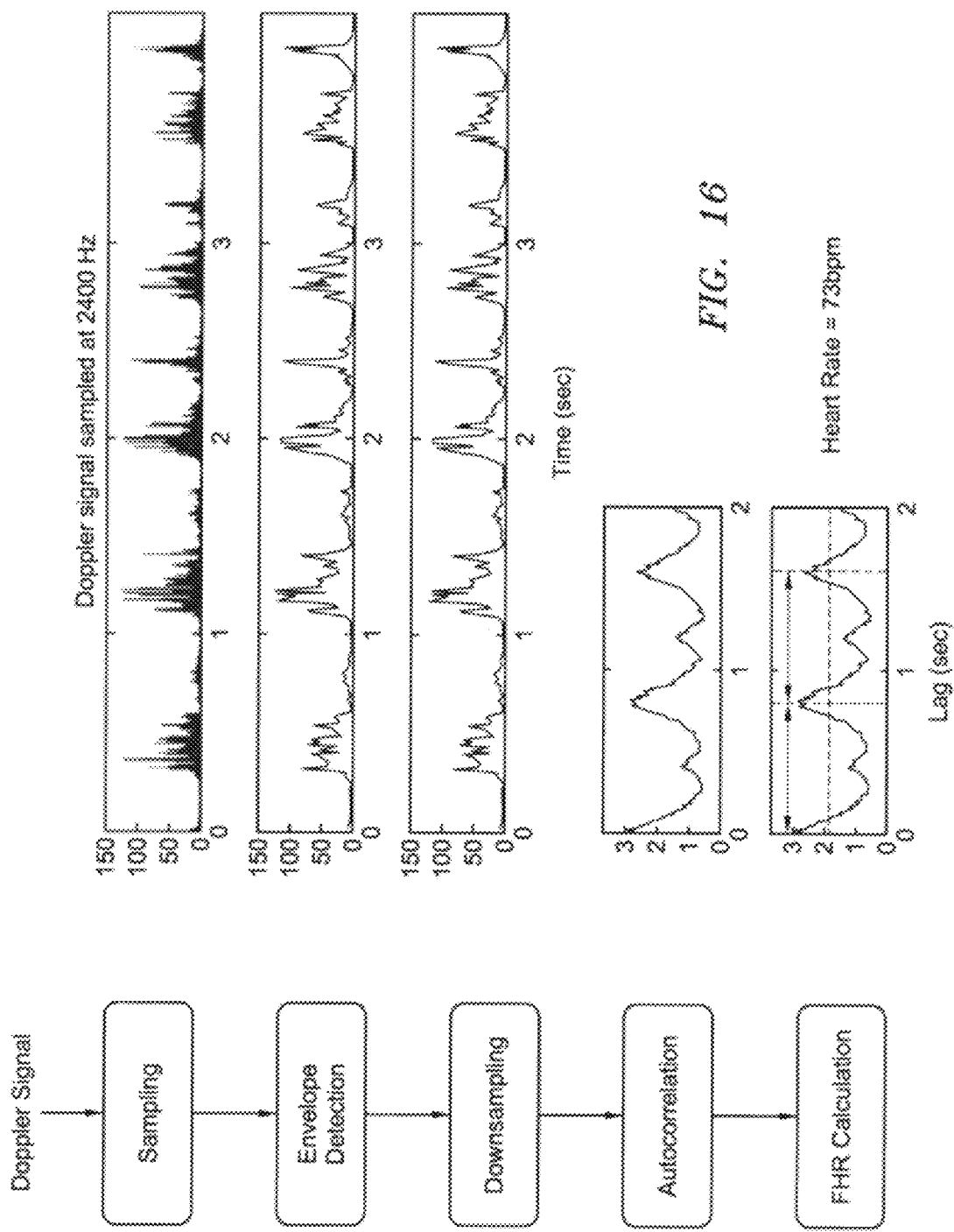
FIG. 16 shows a schematic diagram of the digital signal processing for calculation of FHP from Doppler ultrasound.

An overview of the signal processing algorithms is described. The digital signal processing approach for calculating fetal heart rate (FHR) from Doppler signal has several steps as illustrated in FIG. 16.

Preprocessing includes sampling, envelope detection and downsampling. Performance of the envelope detection depends on how accurately peaks on the Doppler signal are sampled. Therefore, the sampling frequency needs to be high enough to accurately sample peaks in the signal while maintaining the minimum requirement of satisfying the Nyquist criterion. The Doppler signal is sampled at fs=2400 sps to guarantee a precision of 92% in detecting peaks, given a nominal Doppler shift of fd=300 Hz.

The sampled signal is passed through an envelope detection algorithm which detects the positive envelope of the signal. The envelope is then downsampled by a factor of 10, reducing the rate of input data to the autocorrelation algorithm to 240 sps, a sample rate adequate to track the nominal 20 Hz frequency of the envelope to a precision of 96%.

Using autocorrelation, repetitive patterns are found from the Doppler ultrasound signals, and heart rate values are calculated according to the period of peaks in the autocorrelation results. Autocorrelation is a mathematical function that measures the similarity between different segments of a time series signal as a function of time-shift between the segments. Auto-correlation of a signal xt over a window of length W is given by $$r_t(\tau) = \sum_{i=i+1}^{i+W} I_i I_{i+\tau} \quad (1)$$

and is calculated for different values of time lag, τ. Window size is chosen in this work to be 480 samples to ensure that 2 seconds of Doppler data is considered in the autocorrelation calculation, permitting a minimum detectable heart rate of 30 bpm. While a normal fetal heart rate ranges between 110 and 160 bpm, abnormal rates can be as low as 30 bpm or as high as 240. Therefore, the window size used in autocorrelation algorithm needs to be long enough to accommodate at least one heart beat. Furthermore, the window is moved forward over the signal to find repeating patterns. The location of the repeating heart beats appear as peaks in the autocorrelation results which help in finding the duration and subsequently frequency of the heart rates. Thus, the window needs to be moved for a sufficiently long period of time in order to ensure that at least two repetitions of the slowest heart beat (30 bpm) appear in the autocorrelation data. Therefore, the autocorrelation is calculated for τ ranging from 1 to 480.

Occurrence of repeating pattern in the original signal is manifested in the peaks of the autocorrelation results as shown in FIG. 16. Thus, a peak detection algorithm is used to locate peaks in the autocorrelation and calculate heart rate from time duration of the peaks.

For preprocessing, the Doppler signal is sampled at 2400 sps and downsampled to 240 sps for input to the autocorrelation block. While particular design parameters are set forth herein, the particular design parameters may be set by those skilled in the art to achieve the functionality and operations of the inventions described herein.

The choice of sampling frequency relies on two criteria that need to be met: 1) the sampling rate needs to be high enough to satisfy the Nyquist criterion, 2) it needs to be sufficiently high in order to precisely detect peaks of the Doppler signal, which will form the envelope of the signal in subsequent processing block. Studies have shown that in applications of Doppler ultra-sound for fetal heart rate monitoring, the Doppler-shifted signals in the range of 100 to 500 Hz are associated with the baby's heart movements. Therefore, any sampling frequency above 2×500 would satisfy the Nyquist criterion. In other words, fs≥1000.

Figure 17:
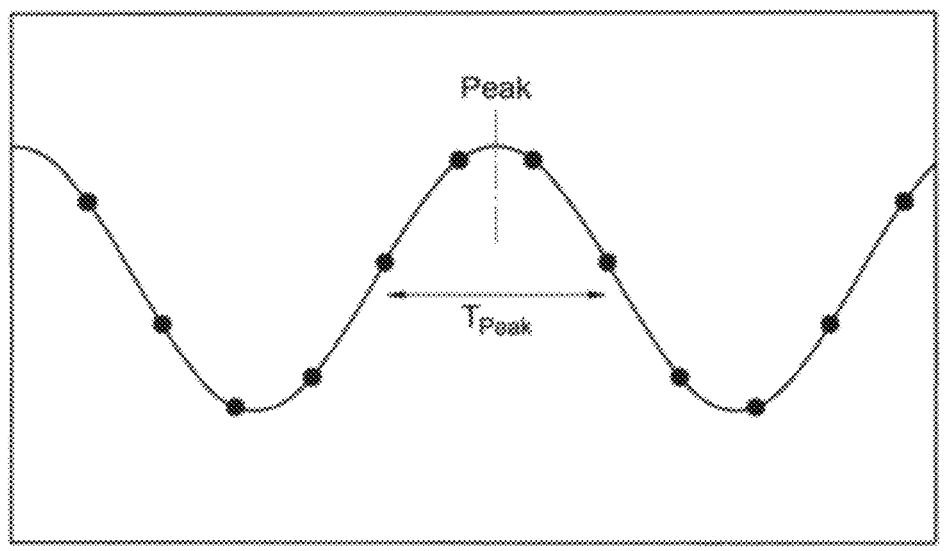
FIG. 17 shows a sampling spaced in the worst case.

In order to explore the second criterion for sampling frequency, the peaks of the Doppler signals approximate a sinusoid of period $2T_{peak}$ as shown in FIG. 17. This shows the samples spaced in the worst case. If samples are spaced by $T_{sample}$, the worst case peak sample is given by $$P = \cos\left(\omega \frac{T_{sample}}{2}\right) = \cos\left(\frac{\pi}{2} \frac{T_{sample}}{T_{peak}}\right) \quad (2)$$

Thus, for a given value of precision, P, $T_{sample}$ can be calculated by $$T_{sample} = \frac{2T_{peak} \cos^{-1}(P)}{\pi} \quad (3)$$

Figure 18:
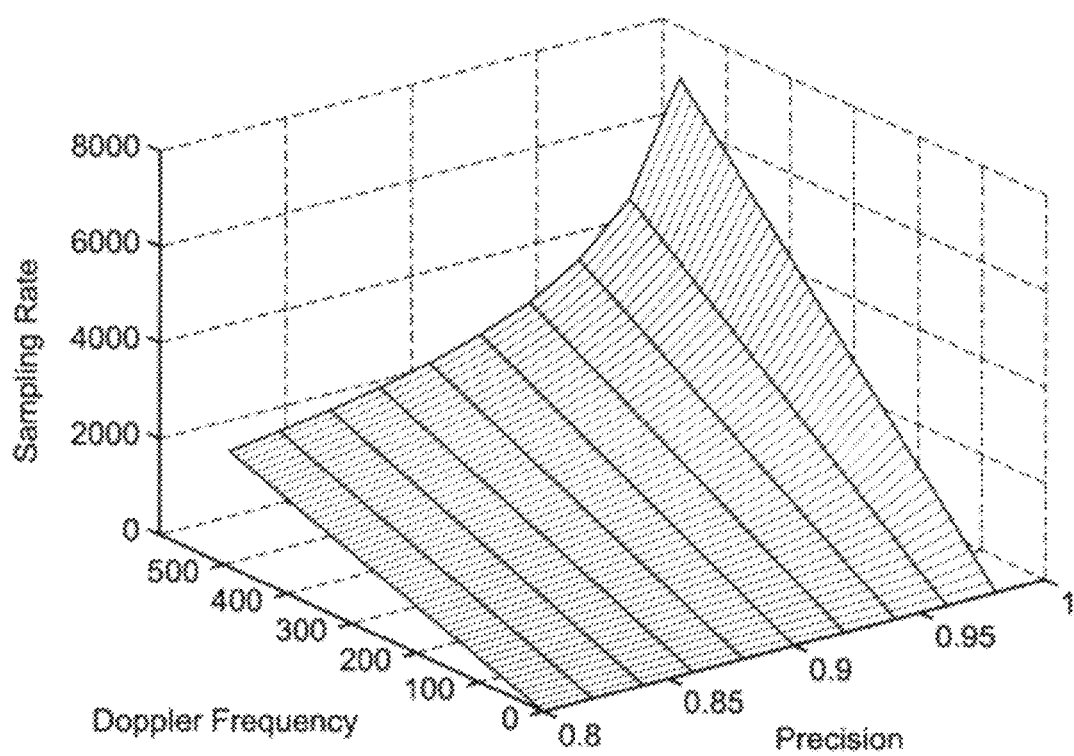
FIG. 18 shows the required sampling rate versus desired precision for varying Doppler frequencies.

FIG. 18 shows required sampling frequency for different precisions and varying Doppler shift frequencies. For the specific application of fetal heart monitoring, a nominal Doppler shift of 300 Hz and precision of 96% results in a sampling rate of 2400 sps.

As to the downsample rate, the preceding approach may be used. The input to the downsampling block is the envelope of the Doppler signal. Experimental data collected from real subjects shows that peaks on the envelope signal has a frequency range between 5 and 20 Hz. Choosing a sampling rate of 240 Hz for downsampled signal gives a downsampling rate of 10. The sampling rate of 240 is adequate to track the nominal 20 Hz frequency of the envelope to a precision of 96% as shown in FIG. 18.

Figure 19:
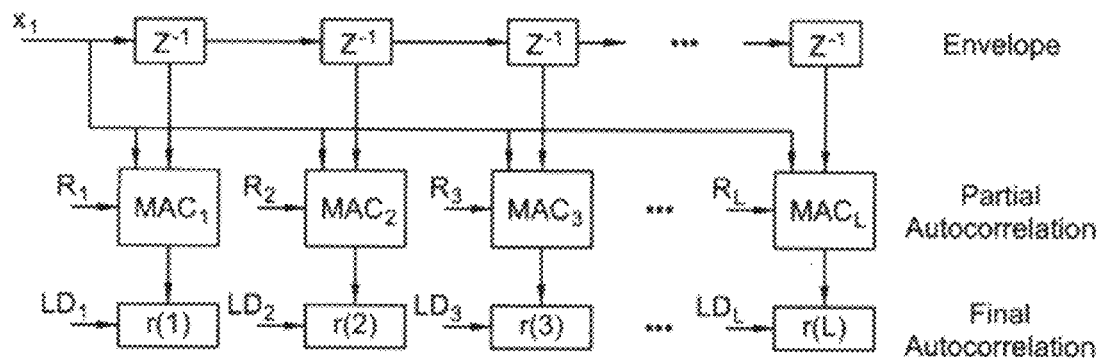
FIG. 19 shows the architecture of the autocorrelation algorithm.

Architecture of the autocorrelation block is illustrated in FIG. 19. This shows an architecture of autocorrelation algorithm with maximum lag=L. The window size (W) is defined by the frequency of reset signal ($R_i$) which is set, for example, every 480 samples resulting in the practical autocorrelation being stored in the final autocorrelation every 2 seconds.

It is a semi-systolic array architecture with the main processing cells being Multiply-ACcumulate (MAC) units that hold partial autocorrelation results. The architecture is composed of 3 register arrays: envelope (top row), partial autocorrelation (middle row), and final autocorrelation (bottom row), each of which has a length of L associated with the maximum lag of $\tau$. Each column of this architecture corresponds to the autocorrelation calculation for a specific $\tau$. For example, the first column calculates autocorrelation for delay of $\tau=1$, second column for delay of $\tau=2$, etc. As shown in the figure, the maximum lag is L samples, which is considered to be L=480 for the experiments as discussed here.

The envelope array stores the last L samples (2 seconds) from envelope and downsampling blocks. Each new downsampled data ($x_i$) is multiplied by each sample in the envelope array and is added to a corresponding location in the partial autocorrelation array. The window size is controlled by the $R_i$ control signals which are activated sequentially ($R_1, R_2, \ldots R_W, R_1, \ldots$). One element of the partial autocorrelation array is copied to its final autocorrelation location for each envelope sample, and partial autocorrelation cell is reset or '0' in preparation for the next series of MAC operations. Given that the length of the autocorrelation array is L=480, each element of the partial correlation is copied/cleared every 2 seconds.

Figure 20:
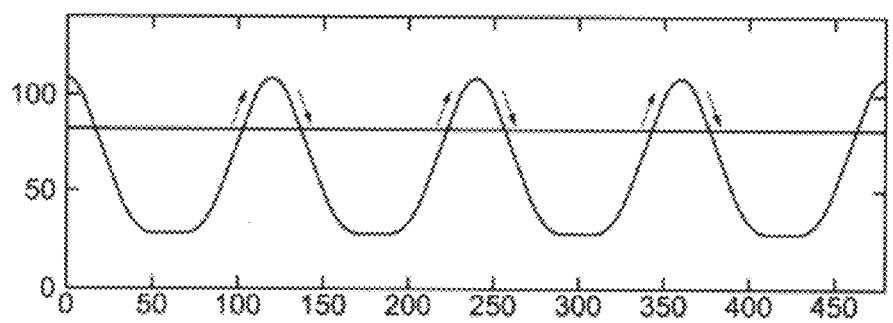
FIG. 20 shows autocorrelation of a synthesized Doppler signal.

A graphic of autocorrelation array ($\tau=\{(1), \tau(2), \ldots, \tau(L)\}$) is shown in FIG. 20, in which a synthesized fetal Doppler signal at 120 bpm was used as input to the system. Because the data is noiseless and perfectly periodic, the results of autocorrelation exhibit clear peaks every 120 samples, i.e. each half second.

A weighted median approach is used to detect the center of each peak, in other words each peak is said to occur at the weighted median of all autocorrelation samples that exceed a certain threshold, as illustrated in the figure. Potentially, there might be more than one peak in the autocorrelation data. The time interval of the heart rate is thus calculated using $$T_{HB} = \frac{\tau \times \sum_{r=1}^{L} r(\tau)}{N_k \times \sum_{r=1}^{L} r(\tau)} \quad (4)$$

$$\forall \, r(\tau) \geq M(1-\epsilon)$$

where $\tau(\tau)$ refers to autocorrelation with lag $\tau$, $M=\tau(1)$ denotes the autocorrelation value at $\tau=1$ and $\epsilon$ is a parameter that specifies the threshold for peak detection, and $N_k$ denotes the peak number, i.e. the peak at 360 samples in the example is the 3rd peak. Peak number is identified by upward and downward threshold crossings, as indicated in the figure.

As suggested by the above equation, the heart rate calculation requires scanning through the entire autocorrelation array of L elements. In the present implementation, one sample of the autocorrelation array ($\tau$) is analyzed during the 2400-sps interrupts, so the entire $\tau$ array is scanned at a rate of 5 times per second, yielding an updated heart rate calculation every 0:2 seconds. Since 2 seconds are required to update the complete array, each heart rate calculation will be based on 10% "new" $\tau$ data and 90% "old" $\tau$ data, which provides a low-pass filter of sorts on the calculated heart rate.

The algorithm for calculating heart rate from the autocorrelation data requires L iterations to complete a full scan of the autocorrelation array. At each iteration of the algorithm, the first autocorrelation value ($\tau(1)$) is read and used to set the threshold since $\tau(1)$ will always have maximum correlation given that $\tau(0)$ is not calculated. A 'peak' is defined as a span of autocorrelation data that exceeds threshold thr=$M(1-\epsilon)$. Within each peak, a summation ($S=\Sigma_\tau r(\tau)$) and weighted summation ($WS=\tau \times \Sigma_\tau r(\tau)$) are calculated, as required for calculation of $T_{peak}$, the weighted median of the peak.

Several tests are then performed to test the validity of the peak. For example, a peak cannot occur less than ¼ of a second after the previous peak or from the beginning of the array, since the device is not sensitive to heart rates >240 bpm. The width of the peak should also exceed a minimum threshold, currently set to 3 samples—such false peaks can be the result of a noisy input. Finally, each valid peak is used to calculate the overall summation (S) and overall weighted summation (WS), which is to calculate $T_{HB}$, and HeartRate (bpm)=60 s/m×240 sps/$T_{HB}$.

This formulation is equivalent to calculating the weighted median of each peak, $T_{peak}$, and then calculating the average of $T_{peak}=N_k$, weighted by their strength S. The most memory consuming blocks in the signal processing pipeline include envelope detection, partial autocorrelation calculation, and final autocorrelation calculation as depicted in FIG. 16. In the design, the Doppler ultrasound is sampled with a resolution of 8 bits with the signal being centered at 0. However, the envelope detection algorithm uses only the positive peaks on the signal to form an envelope of the input. Thus, each element in the envelope array requires only a 7 bit resolution. The partial autocorrelations are calculated by multiplying W elements of the envelope data before flashing the result into the final autocorrelation array. With a window size of W=480 used for autocorrelation calculation, this requires a maximum of 3 bytes for both

TABLE 1

Memory requirement of the algorithm

| Memory Array | Length | Unit Size (bits) | Memory Usage (bytes) |
| --- | --- | --- | --- |
| Envelope | L = 480 | 7 | 420 |
| Partial Autocorrelation | L = 480 | 24 | 1440 |
| Final Autocorrelation | L = 480 | 24 | 1440 |
| Total | | | 3300 |

MAC operations and $\tau$ data are as follows. As shown in Table 1, a total of 3300 bytes memory suffice to accommodate the entire autocorrelation calculation results. The amount of memory required for other computing blocks such as heart rate calculation algorithm described compared to the aforementioned storage is negligible.

For time complexity, major operations which are needed for calculation of the final autocorrelation results are analyzed here. Table 2 shows the number of operations including multiplication, addition (24 bits) and register transfers (move) required to update each one of the

TABLE 2

Number of instructions to process one envelope sample for the purpose of autocorrelation calculation

| Updated Array | #Mult | #Add24 | #Mov |
|---|---|---|---|
| Envelope | 0 | 0 | L |
| Partial Autocorrelation | L | L | 0 |
| Final Autocorrelation | 0 | 0 | 1 |
| #Instructions | L | 6L | L + 1 |
| Total | | 8L + 1 | | arrays during autocorrelation calculations. The envelope array needs L number of register transfer operations in order to shift elements of envelope array upon receiving a new envelope data. Calculation of partial autocorrelation needs multiply-add operations as discussed before. Finally, only one element of final autocorrelation array is updated (transferring results from partial array) when a new envelope data is received. Given that envelope data are generated at a rate of 240 sps, the algorithm requires 921840=240×(8×480+1) instruction per second assuming a length of 480 for each one of the arrays.

While described primarily herein for applications in fetal monitoring, as will be appreciated by those skilled in the art, the applications are much broader. The autocorrelation-based approach for estimating frequency of repeating patterns can be used for a variety of applications in addition to the Doppler ultrasound signal processing. In particular, this technique can be used to measure heart rates from ECG signals, gait parameters such as step rates from motion sensors, and respiration rate from photoplethysmograph (PPG) sensors.

Figure 21:
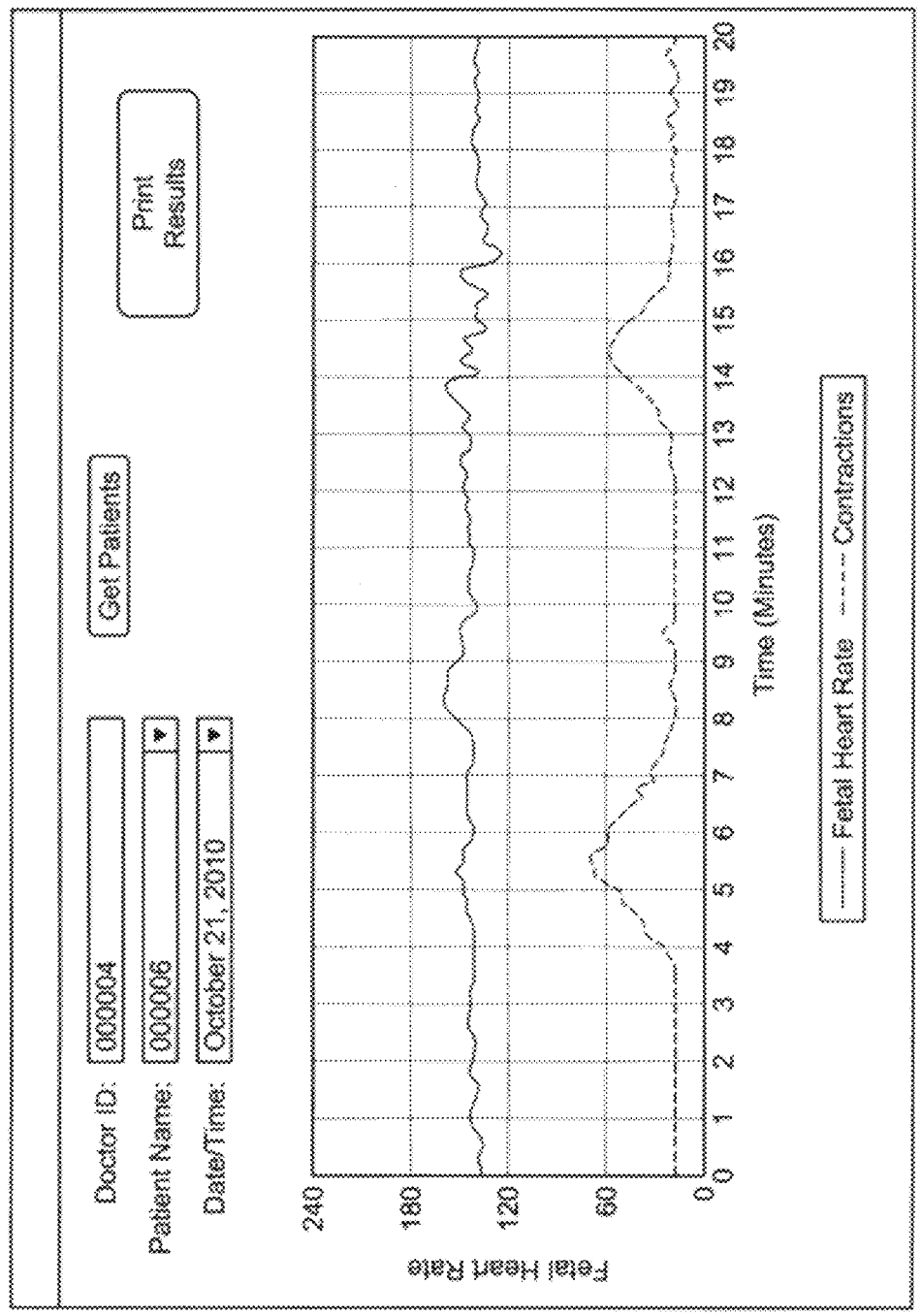
FIG. 21 is a display of an interface displaying, among others, the fetal heart rate and signals corresponding to maternal uterine contractions.

FIG. 21 shows a user interface displaying, among others, the fetal heart rate and signals corresponding to maternal uterine contractions. Various identification information, such as Doctor ID, patient identification and data information may be displayed. The sanitized, HIPAA compliant data is transmitted via secure file transfer protocol to a remote secure server located at a remote location. The server supports a web API for remote data browsing and viewing from any web browser.

Figure 22:
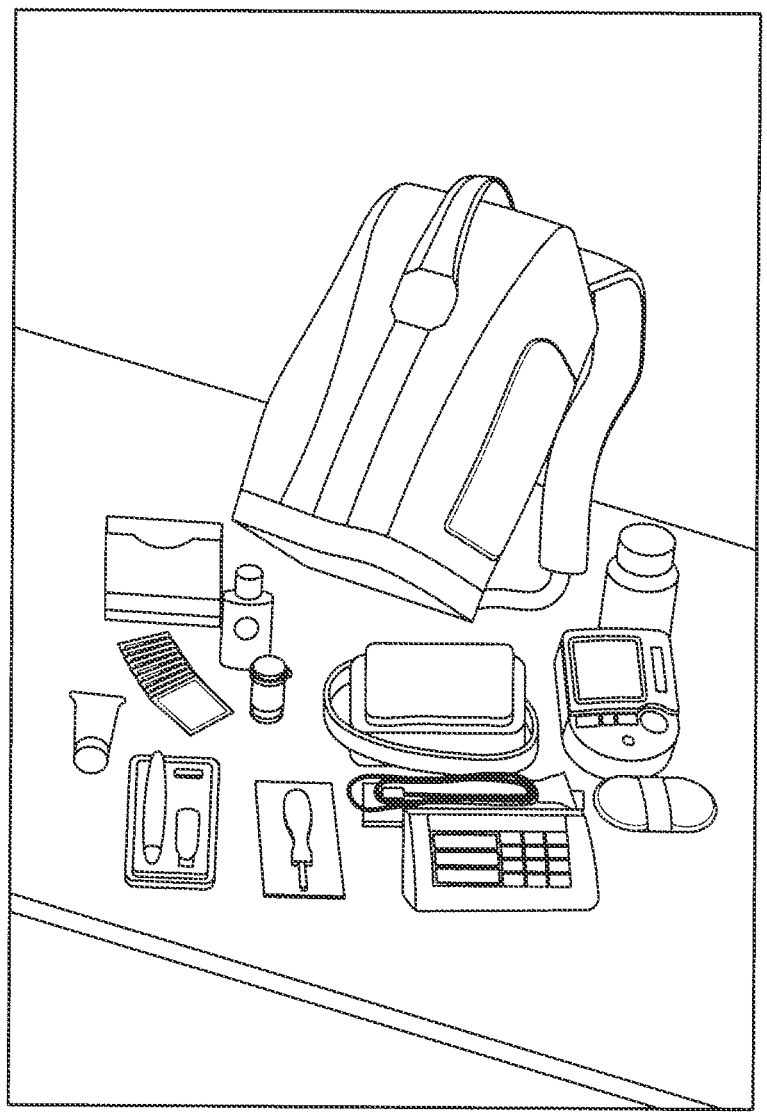
FIG. 22 is a perspective view of the preferred components of the prenatal wireless mobile pack.

FIG. 22 depicts representative components usable with the system or kit. Preferably, a backpack (shown in background) is provided to hold the various other components. A communication device, such as a phone, preferably a smart phone is included (though may optionally be supplied by the patient). An exemplary phone is shown in the foreground. Optionally, a charger and cable may be provided. Other local listening type devices, such as headphones or BLUETOOTH® ear bud, may be provided. Optionally, multiple sized sensors may be provided, such as normal and large. A toco sensor band is supplied, again optionally in multiple sizes, such as small, medium and large.

Various optional blood measurement systems are provided within the system or kit. Blood glucose strips are optionally included. If included, a blood draw tool such as a Lancet, holder, and sharps disposal unit are provided. If ultrasound is to be used, ultrasound gel is optionally provided. Preferably, blood pressure measuring apparatus is provided, including a blood pressure cuff (shown in the center of FIG. 22). Various optional sanitary items may be provided, such as hand sanitizers, alcohol wipes, protective gloves and equipment wipes, e.g., Cava wipes.

Figure 23:
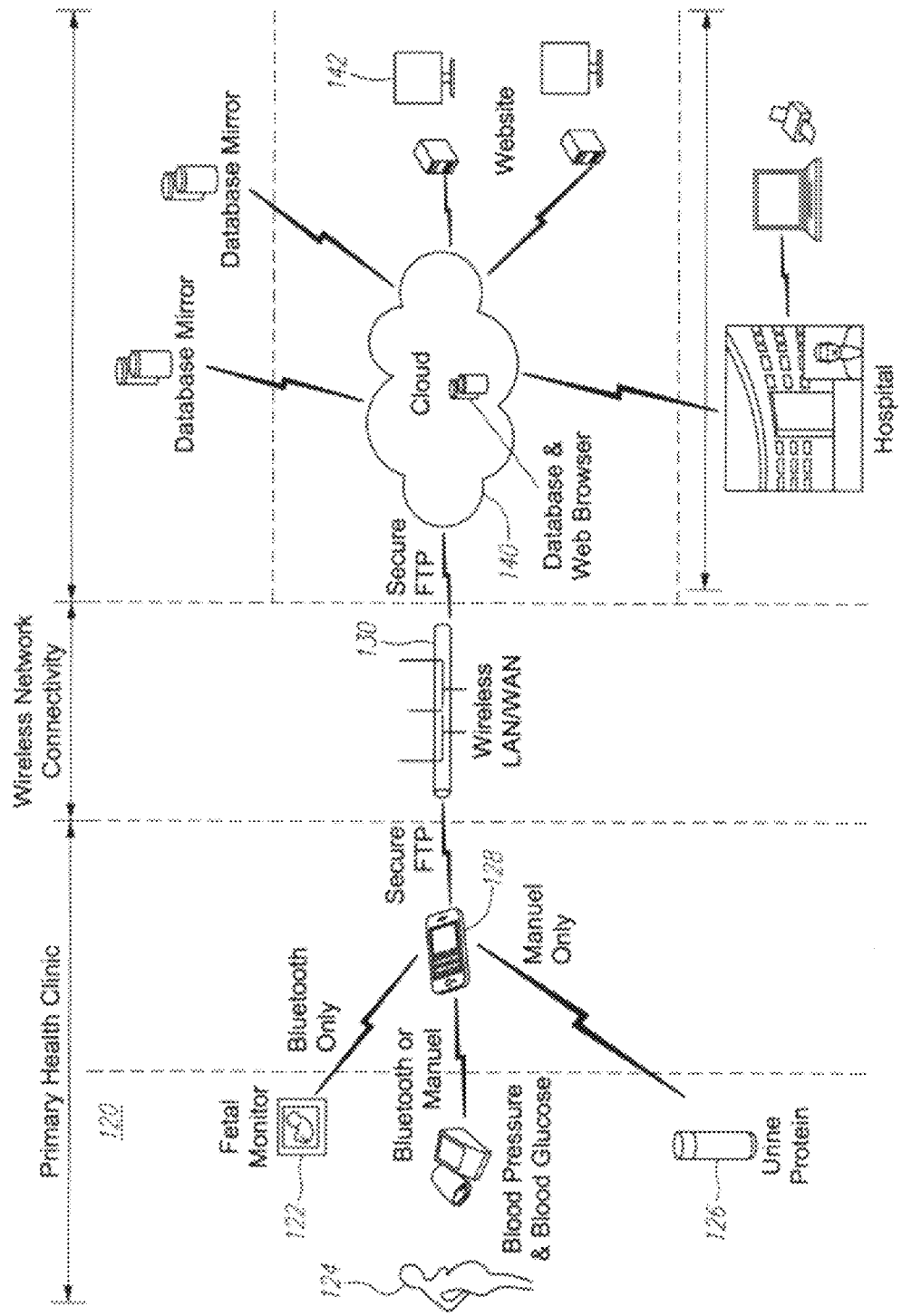
FIG. 23 is a schematic block diagram of the end-to-end solution for the prenatal wireless mobile pack.

FIG. 23 shows an end-to-end system solution for wireless fetal monitoring using the system and kit of this invention. The discussion of cloud computing is applicable, whether in the kit embodiment or a non-kit embodiment, The left-most third 120 of FIG. 23 shows the monitoring location, either a home, a physician's office, remote health clinic or other medical facility. It will be appreciated that any spot at which wireless service is available is compatible with the use of the kit or system. Some or all of the various measurement systems provide output, such as the output of the fetal monitor (toco) 122, blood pressure and blood glucose monitors 124, and urine protein output 126. The measurement systems communicate, preferably via wireless communications technology, to a gateway or hub 128. The communication may be by BLUETOOTH® , or manual, or by any other communication modality consistent with the inventions. Preferably, a display on the device 128, such as a that panel touch screen device, displays information relevant to the outputs of the various measurement systems. As shown in the center third of FIG. 23, wireless network connectivity is utilized. The communications device 128 communicates, in turn, with a communications network 130, such as a wireless LAN/WAN. Preferably, a secure FTP (file transfer protocol) or other communication. modality is used. The data communicated is transmitted within the Telco transport system, which may be wireless, wired or any combination thereof, and use any form of telephony or other communication modality. The right most third of FIG. 23 shows remote computing and processing. The processing may be performed by dedicated hardware and software, or may be a cloud computing system 140, which may include a database and or a web server. Data may then be processed, analyzed and stored at one or more location, and mirrored for redundancy. Preferably, the data is communicated to relevant health care professionals, such as through a web based interface 142. The health care professional may access the data via computer or any handheld type display device. The data and its implications may optionally be communicated back to the patient/mother.

Figure 24:
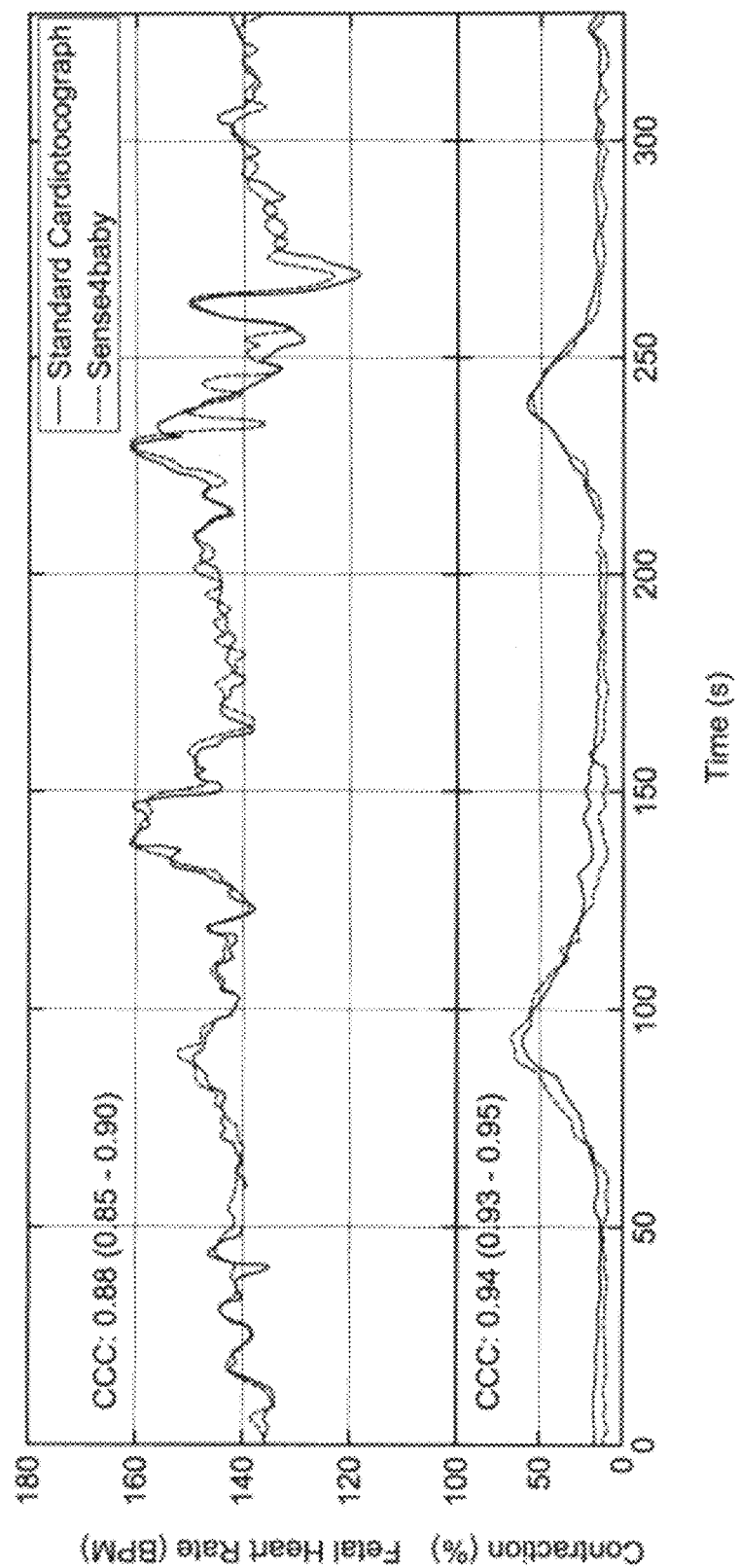
FIG. 24 shows test results in an early laboring patient comparing the subject unit and a standard cardiotocograph.

FIG. 24 shows test results in an early laboring patient comparing the subject unit and a standard cardiotocograph. The upper portion shows the fetal heart rate in beats per minute comparing the results of a standard cardiotocograph with the output of the instant inventions. The bottom portion shows the contraction percentage from a toco transducer. Both graphs are as a function of time in the same scale. This shows a comparison test to verify data for the system against a standard cardiotocograph. It depicts five and half minutes of concurrent monitoring data measured at one sample per second, from a 37-years old pregnant woman at 38.5 weeks gestation age in early labor. System results, extracted from back-end server, favorably match the standard device results. Lin's Concordance Correlation Coefficients (CCC) for heart rate and contraction, were 0.88 (95% confidence range of 0.85-0.90) and 0.94 (95% confidence of 0.93-0.95) which demonstrates close matching between two monitoring devices.

In designs described above, monitoring of electrical activity on the mother's belly could be used for detection of fetal heart beat. This technique eliminates the need for ultrasound transducer and it is less sensitive to the positioning of the device. It is a passive technique, meaning that, unlike ultrasound, the device does not emit any signal for heart beat detection, thus is suitable for continues monitoring.

The other technique for monitoring of the fetal heart beat is using MEMS microphones or microphone arrays to detect the sound of fetal heart. See, e.g., R. R. Lahiji, M. Mehregany, "Microphone Arrays for Listening to Internal Organs of the Body", U.S. Provisional Patent No. 61/258,082, filed November 2009, now published as U.S. Publication 2011-0137209, incorporated herein by reference as if fully set forth herein. This is a passive technique and is suitable for continues monitoring.

Optionally, a manual entry is provided for recording contractions instead of, or in addition to, a toco or uterine EMG recording. If the mother herself senses the uterine contractions and presses a button or actuator on the gateway to record the contraction happening.

All publications and patents cited in this specification are herein incorporated by reference as if each individual publication or patent application were specifically and individually indicated to be incorporated by reference. Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the following claims.

We claim:

1. A wireless fetal and maternal monitoring system comprising:
    a fetal sensor unit adapted to provide signals indicative of a fetal heartbeat,
    a contraction sensor adapted to provide signals indicative of a maternal uterine contraction upon a maternal uterine contraction,
    a digitization and control unit, the digitization and control unit adapted to receive the signals indicative of a fetal heart rate and the signals indicative of a maternal uterine contraction, the digitization and control unit including a heart rate calculation system to calculate the fetal heart rate, a fetal heart rate register for storing the calculated fetal heart rate, a microcontroller configured to refresh per fetal heartbeat the fetal heart rate register, a maternal uterine contraction register to store the signals indicative of maternal uterine contraction, the digitization and control unit providing data fusion by transmitting at least the calculated fetal heart rate from the fetal heart rate register and data based on the signals indicative of the maternal uterine contraction from the maternal uterine contraction register;
    a short-range transmission unit adapted to receive from the digitization and control unit the fused data signals and to retransmit the signals,
    a microphone comprising a maternal heartbeat sensor, and
    a processor including a comparator and a flag memory to eliminate as an erroneous measure a first sensed beat period by comparison to a second sensed beat period and to set a flag in the flag memory.

2. The wireless fetal and maternal monitoring system of claim 1 wherein the fetal sensor unit includes an ultrasound sensor.

3. The wireless fetal and maternal monitoring system of claim 2 wherein the ultrasound sensor is a Doppler ultrasound sensor.

4. The wireless fetal and maternal monitoring system of claim 1 wherein the fetal sensor unit is a sound sensor.

5. The wireless fetal and maternal monitoring system of claim 4 wherein the sound sensor includes a sensor array.

6. The wireless fetal and maternal monitoring system of claim 5 wherein the sensor array is a MEMS microphone array.

7. The wireless and maternal monitoring system of claim 5 wherein the sensor array is a directional sensor array.

8. The wireless fetal and maternal monitoring system of claim 1 wherein the fetal sensor unit includes an ECG sensor.

9. The wireless fetal and maternal monitoring system of claim 1 wherein the short range transmission unit utilizes the BLUETOOTH® standard.

10. The wireless fetal and maternal monitoring system of claim 1 wherein the short range transmission unit operates at a specific absorption rate (SAR) of less than or equal to 0.1 watts/kg.

11. The wireless fetal and maternal monitoring system of claim 1 wherein the short range transmission unit operates at a specific absorption rate (SAR) of less than or equal to 0.05 watts/kg.

12. The wireless fetal and maternal monitoring system of claim 1 wherein the short range transmission unit operates at a specific absorption rate (SAR) of less than or equal to 0.01 watts/kg.

13. The wireless fetal and maternal monitoring system of claim 1 further including an auxiliary communication receiver and transmitter adapted for wearing by the maternal user for receiving transmissions from the short-range transmission.

14. The wireless fetal and Maternal monitoring system of claim 13 wherein the transmissions between the short range transmission unit and the auxiliary communication unit are via a wired connection.

15. The wireless fetal and maternal monitoring system of claim 13 wherein the transmissions between the short range transmission unit and the auxiliary communication unit is wireless.

16. The wireless fetal and maternal monitoring system of claim 13 wherein the auxiliary communication unit is adapted to be worn on a neck.

17. The wireless fetal and maternal monitoring system of claim 1 wherein the contraction sensor is a tocodynamometer sensor.

18. The wireless fetal and maternal monitoring system of claim 1 wherein the contraction sensor includes a button.

19. The wireless fetal and maternal monitoring system of claim 1 wherein short-range transmission unit utilizes the Class 3 BLUETOOTH® standard.

20. The wireless fetal and maternal monitoring system of claim 1 further including a pack adapted to contain one or more of the wireless fetal and maternal monitoring system, a blood pressure device, a glucometer, a reagent dip stick, a cell phone gateway and a wireless hub.

21. The wireless fetal and maternal monitoring system of claim 1 further including a motion sensor.

22. The wireless fetal and maternal monitoring system of claim 1 further including a sensor unit adapted to provide maternal heart rate data.

23. The wireless fetal and maternal monitoring system of claim 1 wherein the data fusion includes data based on signals indicative of a second fetal heart rate.

24. The wireless fetal and maternal monitoring system of claims 1 further including a gateway device, the gateway device including a display to provide for data visualization.

25. The method for measuring fetal and maternal physiological parameters of claim 1 wherein the comparison is of a heartbeat period with a previously stored heartbeat period.

26. The method for measuring fetal and maternal physiological parameters of claim 1 wherein the signal is eliminated if the measured heartbeat period differs from the stored heartbeat period by more than +/−25%.

27. The method for measuring, fetal and maternal physiological parameters of claim 1 wherein the previously stored heart rate is a fetal heartrate.

28. The wireless fetal and maternal monitoring system of claim 1 including a pulse oximeter.

* * * * *